(12) United States Patent
Pereira et al.

(10) Patent No.: US 11,246,583 B2
(45) Date of Patent: Feb. 15, 2022

(54) INSERTION DEVICES, ANCHORS, AND METHODS FOR SECURING AN IMPLANT

(71) Applicant: Boston Scientific Scimed, Inc., Maple Grove, MN (US)

(72) Inventors: Peter J. Pereira, Mendon, MA (US); Jonathan Zoll, Brookline, MA (US); Jozef Slanda, Milford, MA (US); Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 220 days.

(21) Appl. No.: 14/742,065

(22) Filed: Jun. 17, 2015

(65) Prior Publication Data

US 2015/0366555 A1  Dec. 24, 2015

Related U.S. Application Data

(60) Provisional application No. 62/013,913, filed on Jun. 18, 2014.

(51) Int. Cl.
*A61B 17/04* (2006.01)
*A61F 2/00* (2006.01)
(Continued)

(52) U.S. Cl.
CPC ........ *A61B 17/0401* (2013.01); *A61B 17/062* (2013.01); *A61B 17/068* (2013.01);
(Continued)

(58) Field of Classification Search
CPC ............ A61B 17/0401; A61B 17/0643; A61B 2017/0427; A61B 2017/0445;
(Continued)

(56) References Cited

U.S. PATENT DOCUMENTS 342,773 A    6/1886   Bailey
919,138 A    4/1909   Drake et al.
(Continued)

FOREIGN PATENT DOCUMENTS

EP    0140557 A2   5/1985
EP    0589409 A1   3/1994
(Continued)

OTHER PUBLICATIONS

Lieurance et al., "Arthroscopic Knot Tying", retrieved from the Internet: <URL: http://orthonet.on.ca/shoulderscope/arthroscopic knot tying.htm> on Sep. 6, 2006, 7 pages.
(Continued)

*Primary Examiner* — Alexander J Orkin
(74) *Attorney, Agent, or Firm* — Brake Hughes Bellermann LLP

(57) ABSTRACT

In one embodiment, a medical device includes a delivery tool having a carrier member, and a cartridge. The cartridge is coupled to the delivery tool. The cartridge defines an opening. The cartridge is configured to retain an anchor defining a lumen. The carrier member has a retracted configuration and an extended configuration. The carrier member is configured to extend through the lumen defined by the anchor and through the opening defined by the cartridge when the cartridge is coupled to the delivery tool and the carrier member is in its extended configuration.

11 Claims, 42 Drawing Sheets

(51) Int. Cl.
*A61B 17/068* (2006.01)
*A61B 17/062* (2006.01)
*A61B 17/064* (2006.01)
*A61B 17/072* (2006.01)
*A61B 17/00* (2006.01)

(52) U.S. Cl.
CPC ........ *A61B 17/0643* (2013.01); *A61F 2/0004* (2013.01); *A61F 2/0045* (2013.01); *A61B 17/064* (2013.01); *A61B 2017/00805* (2013.01); *A61B 2017/0409* (2013.01); *A61B 2017/0427* (2013.01); *A61B 2017/0464* (2013.01); *A61B 2017/0472* (2013.01); *A61B 2017/0647* (2013.01); *A61B 2017/07271* (2013.01)

(58) Field of Classification Search
CPC .... A61B 2017/0409; A61B 2017/0647; A61B 17/068; A61B 2017/0464; A61F 2/0004; A61F 2/0045
See application file for complete search history.

(56) References Cited

U.S. PATENT DOCUMENTS

| | | |
|---|---|---|
| 1,037,864 A | 9/1912 | Carlson et al. |
| 1,449,087 A | 3/1923 | Bugbee |
| 1,815,725 A | 7/1931 | Pilling et al. |
| 1,822,330 A | 9/1931 | Ainslie |
| 2,577,240 A | 12/1951 | Findley |
| 2,579,192 A | 12/1951 | Kohl |
| 3,013,559 A | 12/1961 | Thomas |
| 3,160,157 A | 12/1964 | Chisman |
| 3,470,875 A | 10/1969 | Johnson |
| 3,557,780 A | 1/1971 | Sato |
| 3,638,653 A | 2/1972 | Berry |
| 3,840,017 A | 10/1974 | Violante |
| 3,918,455 A | 11/1975 | Coplan |
| 3,946,740 A | 3/1976 | Bassett |
| 3,986,468 A | 10/1976 | Szostak et al. |
| 4,161,951 A | 7/1979 | Scanlan, Jr. |
| 4,164,225 A | 8/1979 | Johnson et al. |
| 4,224,947 A | 9/1980 | Fukuda |
| 4,235,177 A | 11/1980 | Arbuckle |
| 4,235,238 A | 11/1980 | Ogiu et al. |
| 4,236,470 A | 12/1980 | Stenson |
| 4,312,337 A | 1/1982 | Donohue |
| 4,345,601 A | 8/1982 | Fukuda |
| 4,451,254 A * | 5/1984 | Dinius ............. A61M 37/0069 206/535 |
| 4,493,323 A | 1/1985 | Albright et al. |
| 4,548,202 A | 10/1985 | Duncan |
| 4,557,265 A | 12/1985 | Andersson |
| 4,579,072 A | 4/1986 | Koike et al. |
| 4,596,249 A | 6/1986 | Freda et al. |
| 4,602,635 A | 7/1986 | Mulhollan et al. |
| 4,612,932 A * | 9/1986 | Caspar ............. A61B 17/0682 206/339 |
| 4,621,640 A | 11/1986 | Mulhollan et al. |
| 4,635,638 A | 1/1987 | Weintraub et al. |
| 4,762,260 A | 8/1988 | Richards et al. |
| 4,781,190 A | 11/1988 | Lee |
| 4,890,615 A | 1/1990 | Caspari et al. |
| 4,898,155 A | 2/1990 | Ovil et al. |
| 4,899,746 A | 2/1990 | Brunk |
| 4,923,461 A | 5/1990 | Caspari et al. |
| 4,926,860 A | 5/1990 | Stice et al. |
| 4,929,239 A * | 5/1990 | Braun ............. A61B 17/0682 221/198 |
| 4,935,027 A | 6/1990 | Yoon |
| 4,957,498 A | 9/1990 | Caspari et al. |
| 5,035,692 A * | 7/1991 | Lyon ............. A61B 17/128 227/901 |
| 5,037,433 A | 8/1991 | Wilk et al. |
| 5,042,707 A | 8/1991 | Taheri |
| 5,047,039 A | 9/1991 | Avant et al. |
| 5,067,957 A | 11/1991 | Jervis |
| 5,100,415 A | 3/1992 | Hayhurst |
| 5,100,418 A | 3/1992 | Yoon et al. |
| 5,100,421 A | 3/1992 | Christoudias |
| 5,100,498 A | 3/1992 | Takeuchi et al. |
| 5,188,636 A | 2/1993 | Fedotov |
| 5,190,560 A * | 3/1993 | Woods ............. A61B 17/122 606/137 |
| 5,254,130 A | 10/1993 | Poncet et al. |
| 5,258,011 A | 11/1993 | Drews |
| 5,281,237 A | 1/1994 | Gimpelson |
| 5,306,281 A | 4/1994 | Beurrier |
| 5,308,353 A | 5/1994 | Beurrier |
| 5,324,298 A | 6/1994 | Phillips et al. |
| 5,336,231 A | 8/1994 | Adair |
| 5,364,408 A | 11/1994 | Gordon |
| 5,386,818 A | 2/1995 | Schneebaum et al. |
| 5,387,221 A | 2/1995 | Bisgaard |
| 5,389,103 A | 2/1995 | Melzer et al. |
| 5,391,174 A | 2/1995 | Weston |
| 5,417,699 A | 5/1995 | Klein et al. |
| 5,417,700 A | 5/1995 | Egan |
| 5,454,823 A | 10/1995 | Richardson et al. |
| 5,458,609 A | 10/1995 | Gordon et al. |
| 5,496,334 A | 3/1996 | Klundt et al. |
| 5,522,820 A | 6/1996 | Caspari et al. |
| 5,527,321 A | 6/1996 | Hinchliffe |
| 5,540,704 A | 7/1996 | Gordon et al. |
| 5,540,705 A | 7/1996 | Meade et al. |
| 5,549,617 A | 8/1996 | Green et al. |
| 5,549,637 A | 8/1996 | Crainich |
| 5,562,686 A | 10/1996 | Sauer et al. |
| 5,573,542 A | 11/1996 | Stevens |
| 5,575,800 A | 11/1996 | Gordon |
| 5,578,044 A | 11/1996 | Gordon et al. |
| 5,591,179 A | 1/1997 | Edelstein |
| 5,593,421 A | 1/1997 | Bauer |
| 5,643,294 A | 7/1997 | Tovey et al. |
| 5,662,664 A | 9/1997 | Gordon et al. |
| 5,662,666 A | 9/1997 | Onuki et al. |
| 5,665,096 A | 9/1997 | Yoon |
| 5,690,653 A | 11/1997 | Richardson et al. |
| 5,700,272 A | 12/1997 | Gordon et al. |
| 5,700,273 A | 12/1997 | Buelna et al. |
| 5,713,910 A | 2/1998 | Gordon et al. |
| 5,741,277 A | 4/1998 | Gordon et al. |
| 5,741,279 A | 4/1998 | Gordon et al. |
| 5,746,753 A | 5/1998 | Sullivan et al. |
| 5,755,727 A | 5/1998 | Kontos |
| 5,759,188 A | 6/1998 | Yoon |
| 5,779,718 A | 7/1998 | Green et al. |
| 5,782,845 A | 7/1998 | Shewchuk |
| 5,827,298 A | 10/1998 | Hart et al. |
| 5,843,001 A | 12/1998 | Goldenberg |
| 5,855,585 A | 1/1999 | Kontos |
| 5,860,992 A | 1/1999 | Daniel et al. |
| 5,899,909 A | 5/1999 | Claren et al. |
| 5,904,692 A | 5/1999 | Steckel et al. |
| 5,908,428 A | 6/1999 | Scirica et al. |
| 5,910,148 A | 6/1999 | Reimels et al. |
| 5,911,727 A | 6/1999 | Taylor |
| 5,919,199 A | 7/1999 | Mers Kelly et al. |
| 5,951,575 A | 9/1999 | Bolduc et al. |
| 5,954,732 A | 9/1999 | Hart et al. |
| 6,048,351 A | 4/2000 | Gordon et al. |
| 6,051,006 A | 4/2000 | Shluzas et al. |
| 6,074,418 A * | 6/2000 | Buchanan ............. A61B 17/064 623/2.11 |
| 6,117,067 A | 9/2000 | Gil-Vernet |
| 6,224,525 B1 | 5/2001 | Stein |
| 6,443,962 B1 | 9/2002 | Gaber |
| 6,454,778 B2 | 9/2002 | Kortenbach |
| 6,743,239 B1 | 6/2004 | Kuehn et al. |
| 6,830,578 B2 | 12/2004 | O'Heeron et al. |
| 6,936,054 B2 * | 8/2005 | Chu ............. A61B 17/0469 606/144 |
| 7,041,111 B2 | 5/2006 | Chu |

(56) References Cited

U.S. PATENT DOCUMENTS

| | | | |
|---|---|---|---|
| 7,166,116 B2* | 1/2007 | Lizardi | A61B 17/0469 606/144 |
| 8,709,021 B2 | 4/2014 | Chu et al. | |
| 9,089,262 B2* | 7/2015 | Hashiba | A61B 17/0625 |
| 9,144,483 B2 | 9/2015 | Chu | |
| 2003/0023248 A1* | 1/2003 | Parodi | A61B 17/064 606/139 |
| 2003/0045900 A1 | 3/2003 | Hahnen et al. | |
| 2003/0181924 A1* | 9/2003 | Yamamoto | A61B 17/0467 606/144 |
| 2003/0208209 A1* | 11/2003 | Gambale | A61B 17/00234 606/144 |
| 2003/0233104 A1 | 12/2003 | Gellman et al. | |
| 2003/0236536 A1* | 12/2003 | Grigoryants | A61B 17/0469 606/151 |
| 2004/0010245 A1* | 1/2004 | Cerier | A61B 17/00234 606/1 |
| 2004/0138682 A1 | 7/2004 | Onuki et al. | |
| 2004/0147941 A1* | 7/2004 | Takemoto | A61B 17/0467 606/144 |
| 2004/0230198 A1* | 11/2004 | Manzi | A61B 17/8852 606/90 |
| 2005/0177181 A1* | 8/2005 | Kagan | A61F 5/0076 606/151 |
| 2005/0251167 A1 | 11/2005 | Voegele et al. | |
| 2006/0041263 A1 | 2/2006 | Chu et al. | |
| 2006/0253131 A1* | 11/2006 | Wolniewicz, III | A61B 17/10 606/142 |
| 2007/0088390 A1* | 4/2007 | Paz | A61B 17/0401 606/232 |
| 2007/0276412 A1 | 11/2007 | Catanese et al. | |
| 2008/0087703 A1* | 4/2008 | Bailly | A61B 17/0401 227/67 |
| 2009/0093824 A1* | 4/2009 | Hasan | A61B 17/0401 606/139 |
| 2010/0240951 A1* | 9/2010 | Catanese, III | A61B 17/0401 600/104 |
| 2011/0130773 A1* | 6/2011 | Saliman | A61B 17/0469 606/145 |
| 2012/0089181 A1* | 4/2012 | Shanley | A61B 17/0057 606/223 |
| 2013/0112731 A1* | 5/2013 | Hodgkinson | A61B 17/105 227/176.1 |
| 2014/0088621 A1* | 3/2014 | Krieger | A61B 17/0469 606/153 |
| 2014/0166514 A1* | 6/2014 | Martin | A61B 17/0483 206/365 |
| 2014/0209660 A1* | 7/2014 | Rogers | A61B 17/0401 227/176.1 |
| 2014/0236193 A1* | 8/2014 | Chin | A61B 17/0401 606/145 |

FOREIGN PATENT DOCUMENTS

| | | |
|---|---|---|
| EP | 0674875 A1 | 10/1995 |
| GB | 2268690 A | 1/1994 |
| WO | 19901003766 A1 | 4/1990 |
| WO | 19921012674 A1 | 8/1992 |
| WO | 19931001750 A1 | 2/1993 |
| WO | 19941005213 A1 | 3/1994 |
| WO | 19941013211 A1 | 6/1994 |
| WO | 19961009796 A2 | 4/1996 |
| WO | 19961027331 A1 | 9/1996 |
| WO | 19981048713 A1 | 11/1998 |
| WO | 19991047050 A2 | 9/1999 |
| WO | 20011028432 A1 | 4/2001 |
| WO | 2001/066018 A1 | 9/2001 |
| WO | 20031105701 A2 | 12/2003 |
| WO | 2015/195897 A1 | 12/2015 |

OTHER PUBLICATIONS

Dr. Roberts, "Human Gross Anatomy and Embryology Pelvic Organs and Pelvic Diaphragm" Lecture at University of Minnesota Medical School in 2000, retrieved on Feb. 7, 2003, 6 pages.

"GyneFlex™—Instructions: Female Pelvic Floor Muscles", shows color diagrams of the pelvic floor area, retrieved on Feb. 7, 2003, 4 pages.

"Physicians/Plastic Surgety/Pelvic Floor Dysfunction", Abington Memorial Hospital, describe what the pelvic area constitutes, retrieved on Feb. 6, 2003, 2 pages.

International Search Report for International Patent Application No. PCT/US2003/18486, dated Jan. 27, 2004, 7 pages.

Capio CL Transvaginal Suture Capturing Device Product Brochure: "Transvaginal Suture Fixation to Cooper's Ligament for Sling Procedure", Boston Scientific Corporation, 2000, pp. 1-4.

Capio Suture Capturing Device Product Brochure: "Reach, Throw and Capture: One Step. One Device", Boston Scientific Corporation, 1998, pp. 1-4.

International Search Report for International Patent Application No. PCT/US2007/083617, dated Apr. 2, 2008, 3 pages.

Guillonneau et al., "Laparoscopic Radical Prostatectomy", Computer Motion, Santa Barbara, CA, Jan. 2000, pp. 1-12.

International Search Report and Written Opinion for PCT Patent Application No. PCT/US2015/036402, dated Sep. 10, 2015, 13 pages.

International Preliminary Report for PCT Application No. PCT/US2016/036402, dated Dec. 29, 2016, 8 pages.

* cited by examiner

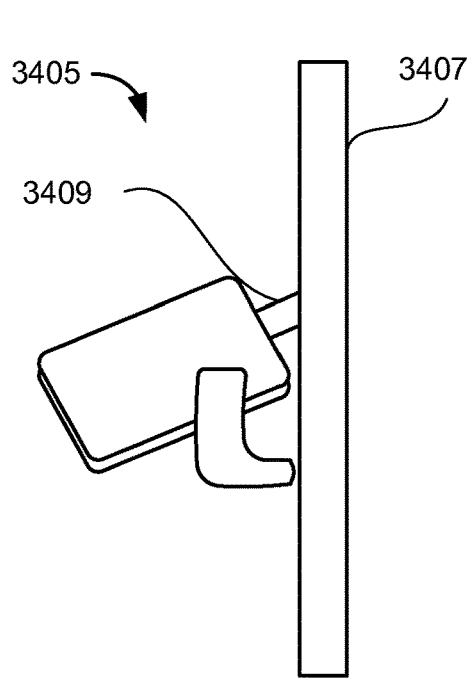
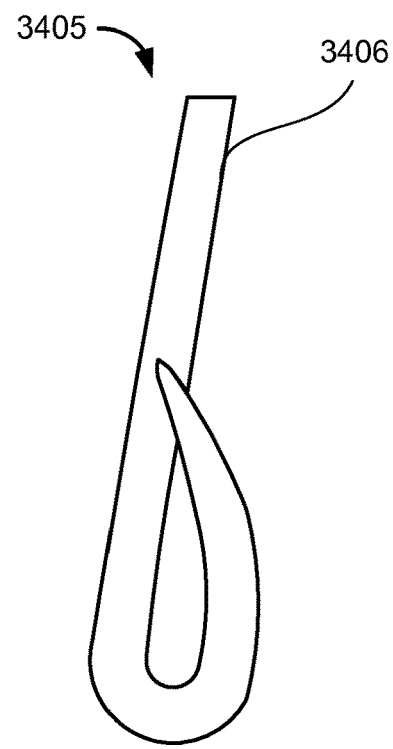
FIG. 34
FIG. 35
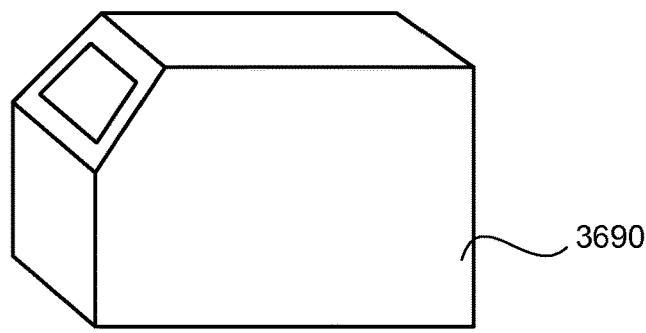
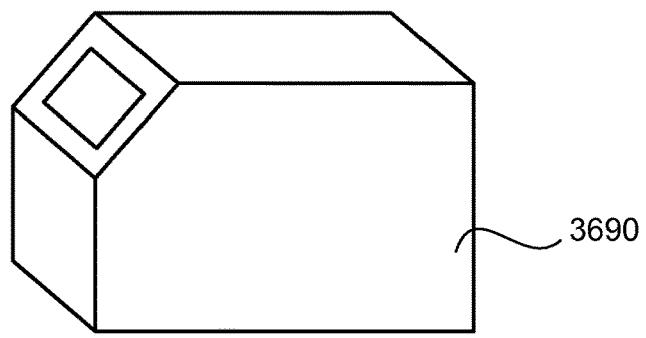
FIG. 36

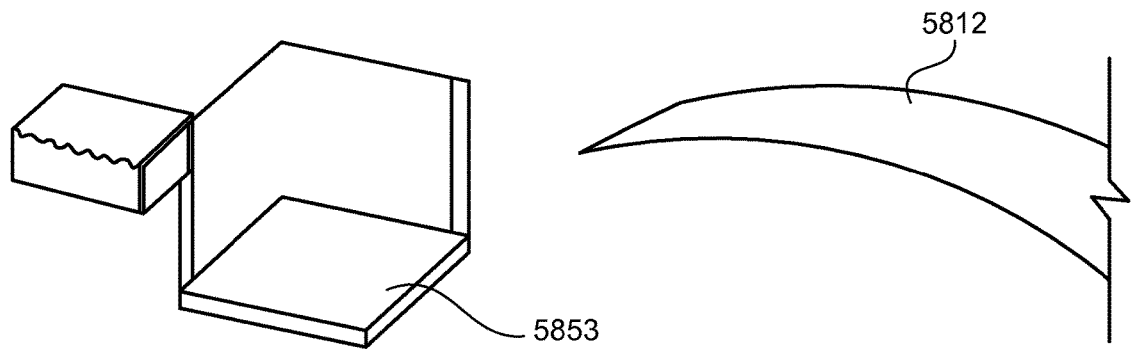
FIG. 58
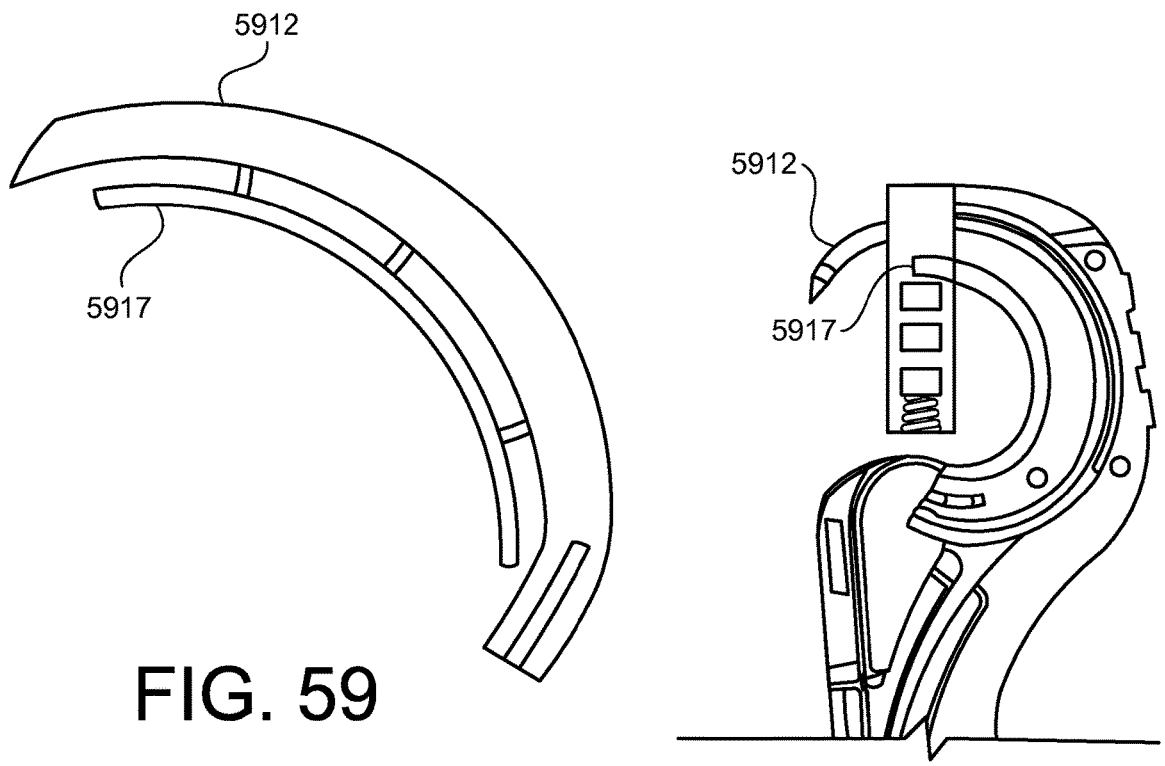
FIG. 59
FIG. 60

INSERTION DEVICES, ANCHORS, AND METHODS FOR SECURING AN IMPLANT

CROSS-REFERENCE TO RELATED APPLICATION

This application is a Nonprovisional of, and claims priority to, U.S. Patent Application No. 62/013,913, filed on Jun. 18, 2014, entitled "INSERTION DEVICES, ANCHORS, AND METHODS FOR SECURING AN IMPLANT", which is incorporated by reference herein in its entirety.

TECHNICAL FIELD

This disclosure relates generally to medical devices and more particularly to devices that are configured to help secure an implant within a body of a patient and methods for placing such devices within the body of the patient.

BACKGROUND

A variety of medical procedures are performed to provide support to portions of a body of a patient. For example, some medical procedures are performed to treat various female pelvic dysfunctions, including procedures to treat urinary incontinence, and correcting various prolapse conditions such as uterine prolapse, cystoceles, rectoceles, and vaginal vault prolapse.

Women often experience vaginal prolapses due to age or other factors. For example, women may experience a cystocele, a rectocele and/or a hysterocele. A cystocele occurs when the bladder bulges into the vagina, and a rectocele occurs when the rectum bulges into the vagina. A hysterocele occurs when the uterus descends into the vagina. An enterocele (small bowel prolapse) can also occur, when the small bowel pushes through the upper wall of the vagina.

Treatments of such dysfunctions have included suturing procedures or the use of implants for support or suspension of a portion of a body of a patient. For example, a hysterocele is often treated with a hysterectomy followed by a vaginal vault suspension. In some cases a sacrocolpopexy may be performed. Various devices and procedures are used to deliver and secure pelvic implants within a variety of different anatomical structures within a pelvic region. Implants can be delivered to a pelvic region through one or more vaginal incisions, and/or through exterior incisions in the patient.

Existing implants differ in many ways including size, shape, material, number and location of straps, and in the method in which they are delivered and placed within a pelvic region. Additionally, depending on the particular condition to be treated and the implant used, pelvic floor repair can require various fixation locations within a pelvic region. For example, an implant can be secured using a number of anchors disposed at various fixation points.

It may be difficult to secure the implants within body of the patient at the various attachment locations.

SUMMARY

In one embodiment, a medical device includes a delivery tool having a carrier member, and a cartridge. The cartridge is coupled to the delivery tool. The cartridge defines an opening. The cartridge is configured to retain an anchor defining a lumen. The carrier member has a retracted configuration and an extended configuration. The carrier member is configured to extend through the lumen defined by the anchor and through the opening defined by the cartridge when the cartridge is coupled to the delivery tool and the carrier member is in its extended configuration.

In some embodiments, the cartridge defines a cavity being configured to retain the anchor. In some embodiments, the cartridge is configured to retain a plurality of anchors. In some embodiments, the delivery tool includes an actuation member configured to move the carrier member from its retracted configuration to its extended configuration. In some embodiments, the carrier member is retracted form the cartridge when the carrier member is in its refracted configuration. In some embodiments, the cartridge is fixedly coupled to the delivery tool. In some embodiments, the cartridge is removably coupled to the delivery tool. In some embodiments, the cartridge is integrally formed with at least a portion of the delivery tool. In some embodiments, the delivery tool includes a projection, the cartridge defines an aperture, the projection being configured to at least partially extend into the aperture to help removably couple the cartridge to the delivery tool.

A medical device of the type described here may, in some embodiment, include a delivery tool, an anchor and a catch. In these embodiments, the delivery tool has a carrier member. The anchor is removably coupled to the delivery tool. The catch is removably coupled to the delivery tool. The carrier member has a retracted configuration and an extended configuration. The carrier member is configured to move the anchor towards the catch when the carrier moves from its retracted configuration to its extended configuration.

In some embodiments, the anchor defines a lumen and the carrier is configured to extend through the lumen defined by the anchor. In some embodiments, the delivery tool includes a cartridge configured to retain the anchor. In some embodiments, the delivery tool includes a cartridge configured to retain the anchor and the catch. In some embodiments, the delivery tool includes a first cartridge and a second cartridge, the first cartridge being configured to retain the anchor, the second cartridge being configured to retain the catch. In some embodiments, the delivery tool includes a cartridge, the cartridge being configured to retain the anchor, the cartridge being configured to be removably coupled to the delivery tool. In some embodiments, the delivery tool includes a cartridge, the cartridge being configured to retain the anchor, the cartridge being integrally formed with at least a portion of the delivery tool. In some embodiments, the anchor is configured to be coupled to the catch. In some embodiments, the device includes a filament having a first end portion coupled to the anchor and a second end portion coupled to the catch.

In another embodiment, a method of securing an implant within a body of a patient includes inserting a device into a body of the patient, the device having a delivery tool, an anchor and a catch, the delivery tool including a carrier member, the anchor being removably coupled to the delivery tool, the catch being removably coupled to the delivery tool; passing the anchor through the implant and through bodily tissue; coupling the anchor to the catch; removing the anchor from the delivery tool; and removing the catch from the delivery tool.

In some embodiments, the method includes removing the delivery tool from the body of the patient.

BRIEF DESCRIPTION OF THE DRAWINGS

FIG. 4 is a perspective view of the distal portion of the medical device of FIG. 2 with a portion of the device shown in see-through.

FIG. 6 is a perspective view of a distal portion of the medical device of FIG. 2 with portions of the device shown in see-through.

FIGS. 34 and 35 illustrate a cam system according to an embodiment of the invention.

FIG. 36 illustrate a series of anchors according to an embodiment of the invention.

FIG. 58 is a perspective view of a portion of a carrier according to an embodiment of the invention.

FIG. 59 is a perspective view of a carrier according to an embodiment of the invention.

FIG. 60 is a perspective view of medical device according to an embodiment of the invention.

DETAILED DESCRIPTION

Figure 1:
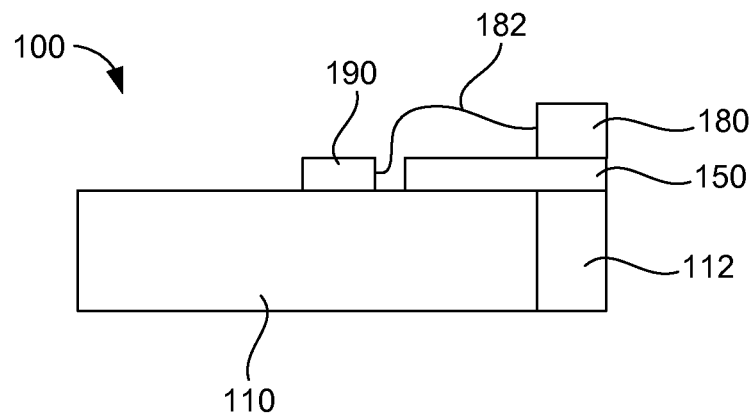
FIG. 1 is a schematic illustration of a device according to an embodiment of the invention.

The devices and methods described herein are generally directed to implants configured to be disposed within a body of a patient. In some embodiments, the implants are pelvic implants (e.g., posterior support implants, anterior support implants, total pelvic floor repair implants) and the delivery and placement of such implants within a pelvic region (also referred to herein as "pelvis") of a patient. An implant can be placed into the pelvic space of a patient and secured at any of several locations within the pelvic space to treat many different pelvic floor dysfunctions. For example, an implant can be secured to a vaginal wall or vaginal tissue proximate a vaginal wall, a sacrospinous ligament, or a ureterosacral ligament for uterine preservation (e.g., if a prolapsed uterus is otherwise healthy, a hysterectomy is not preformed and the uterus is re-suspended with an implant), or for posterior support. In another embodiment, an implant can be secured to pubo-urethral tissue or an obturator muscle (e.g., internus or externus) or membrane (each also referred to herein as "obturator") to treat, for example, incontinence. In yet another embodiment, an implant can be secured to a sacrospinous ligament or an arcus tendineus fascia pelvis (i.e., white line) (also referred to herein as "arcus tendineus") for paravaginal repairs including, for example, cystoceles, rectoceles and enteroceles. An implant can also be secured to various combinations of such locations. A single implant or multiple implants can be used in a single procedure. In some applications, when multiple implants are used, support can be provided in desired areas and improved control of the direction of stretch or support of the implant can be achieved. Various delivery devices, delivery aids, and methods are also described for delivering and securing an implant assembly within the patient. The implants and procedures described herein may be used in a female patient or a male patient.

An implant according to an embodiment of the invention can be implanted, for example, through a vaginal incision, in a retro-pubic direction (behind the pubic bone), or in a pre-pubic direction (in front of the pubic bone). In other embodiments, an implant can be placed in the direction of other anatomical structures or tissues as desired. A procedure to deploy a pelvic implant can include vaginal incisions, such as an anterior vaginal incision and/or an anterior vaginal incision. In some embodiments, a procedure may include an exterior incision.

The implants described herein can be delivered to various parts of the body of the patient using a variety of different method and delivery devices. The implants and methods disclosed herein include pelvic floor implants, but the implants may be configured to be placed and methods may be used to place such implants in any portion of the body of the patient.

The terms proximal and distal described in relation to various devices, apparatuses, and components as discussed in the subsequent text of the present invention are referred with a point of reference. The point of reference, as used in this description, is a perspective of an operator. The operator may be a surgeon, a physician, a nurse, a doctor, a technician, and the like who may perform the procedure and operate the medical device as described in the present invention. The term proximal refers to an area or portion that is closer or closest to the operator during a surgical procedure. The term distal refers to an area or portion that is farther or farthest from the operator.

An implant can be delivered to a pelvic region of a patient using a variety of different delivery devices, only some examples of which are described herein.

FIG. 1 is a schematic illustration of a medical device 100 according to an embodiment of the invention. The medical device 100 includes a delivery tool 110 and a cartridge 150 coupled to the delivery tool 110.

The delivery tool 110 includes a carrier member 112 that is movably coupled to a body portion of the delivery tool 110. Specifically, the carrier member 112 may be moved from a first position with respect to the body portion of the delivery tool 110 to a second position with respect to the body portion. In some embodiments, the carrier member 112 may be placed or moved into more than two positions with respect to the body portion. For example, the carrier member 112 may be configured to be moved into three, four, five, or any other number of different positions with respect to the body portion.

The cartridge 150 is coupled to the delivery tool 110. In some embodiments, the cartridge 150 is fixedly coupled delivery tool. For example, in such embodiments, the cartridge 150 may be unitarily or monolithically formed with the delivery tool 110 or a portion of the delivery tool 110. In other embodiments, the cartridge 150 may be removably coupled to the delivery tool 110. For example, in such embodiments, the cartridge 150 may be selectively coupled to or removed from the delivery tool 110. In some embodiments, the cartridge 150 may include or define an engagement member that is configured to engage a portion of the delivery tool 110 to removably couple or help couple the cartridge 150 to the delivery tool 110.

The cartridge 150 is configured to retain an anchor or anchor member 180. For example, in some embodiments, the cartridge 150 defines a cavity that is configured to receive, house, or retain the anchor 180. In some embodiments, the cartridge 150 is configured to retain more than one anchor or anchor member simultaneously.

In the illustrated embodiment, the medical device 100 includes a catch or catch member 190. The catch or catch member 190 is removably coupled to the delivery tool 110. In some embodiments, the catch 190 is disposed within or retained by a cartridge. For example, in some embodiments, the catch 190 is disposed within or retained by the cartridge 150. In other embodiments, the catch 190 is disposed within or retained by a second cartridge. In some embodiments, the catch 190 is removably coupled to the delivery tool 110 without the use of a cartridge. The catch or catch member 190 is configured to be coupled to the anchor 180. For example, in some embodiments, the catch or catch member 190 defines an opening or cavity and is configured to receive at least a portion of the anchor 180.

In the illustrated embodiment, the anchor 180 is attached to the catch 190 via an attachment member 182. In some embodiments, the attachment member 182 is a filament, a suture, an elastic member or other type of line or structure that is configured to extend from the anchor 180 to the catch 190. In some embodiments, the attachment member 182 is a suture that has a first end portion coupled to the anchor 180 and a second end portion coupled to the catch 190.

In some embodiments, the cartridge 150 allows the carrier 112 to access the anchor 180. For example, in some embodiments, the cartridge 150 defines an opening. The carrier 112 is configured to access the anchor 180 via the opening. For example, in some embodiments, the carrier 112 is configured to extend into or through the opening of the cartridge 150 to access or otherwise engage the anchor 180. In some embodiments, the anchor 180 defines a lumen. In some such embodiments, the carrier 112 is configured to extend into or through the lumen defined by the anchor.

In some embodiments, the carrier 112 is configured engage the anchor to move the anchor 180 out of or away from cartridge 150. For example, some embodiments, the carrier 112 is configured to move from a first or retracted position to a second or extended position. The carrier 112 is configured to move the anchor 180 away from the cartridge when or as the carrier moves to its second or extended position or configuration. In some embodiments, the carrier 112 is configured to move the anchor 180 toward the catch 190 as the carrier 112 moves from its first position to its second position. In some embodiments, the carrier 112 is configured to move the anchor 180 away from the cartridge 150 and towards the catch 190 such that the anchor 180 engages and is coupled to the catch 190.

In some embodiments, the medical device 100 may be inserted into the body of the patient such that the anchor 180 and the catch 190 are disposed on opposite sides of bodily tissue (or such that some bodily tissue is disposed between the anchor 180 and the catch 190). In some embodiments, the device 100 may be used to secure or help secure an implant within a body of the patient. In some such embodiments, the medical device 100 may be inserted into a body of a patient such that bodily tissue and a portion of the implant are disposed between the anchor 180 and the catch 190.

The carrier 112 can then be moved from its first or retracted position to its second or extended configuration. As the carrier 112 is moved from its first position to its second position, the carrier 112 will engage the anchor 180, pass the anchor through the bodily tissue (and the implant) and into the catch 190 such that the anchor 180 is coupled to the catch 190. The carrier 112 can then be retracted back to its first or retracted position, leaving the anchor 180 coupled to the catch 190. The catch 190 can then be removed from the delivery tool 110 and the delivery tool 110 can be removed from the body of the patient thereby leaving the anchor 180 and the catch 190 disposed within the body of the patient. In the illustrated embodiment, when the anchor 180 is passed through bodily tissue (and an implant) and is coupled to the catch 190 (as described above), the catch 190, anchor 180, and attachment member 182 will collectively form a loop or circle about the tissue and implant to couple or help couple the implant to the bodily tissue.

Figure 2:
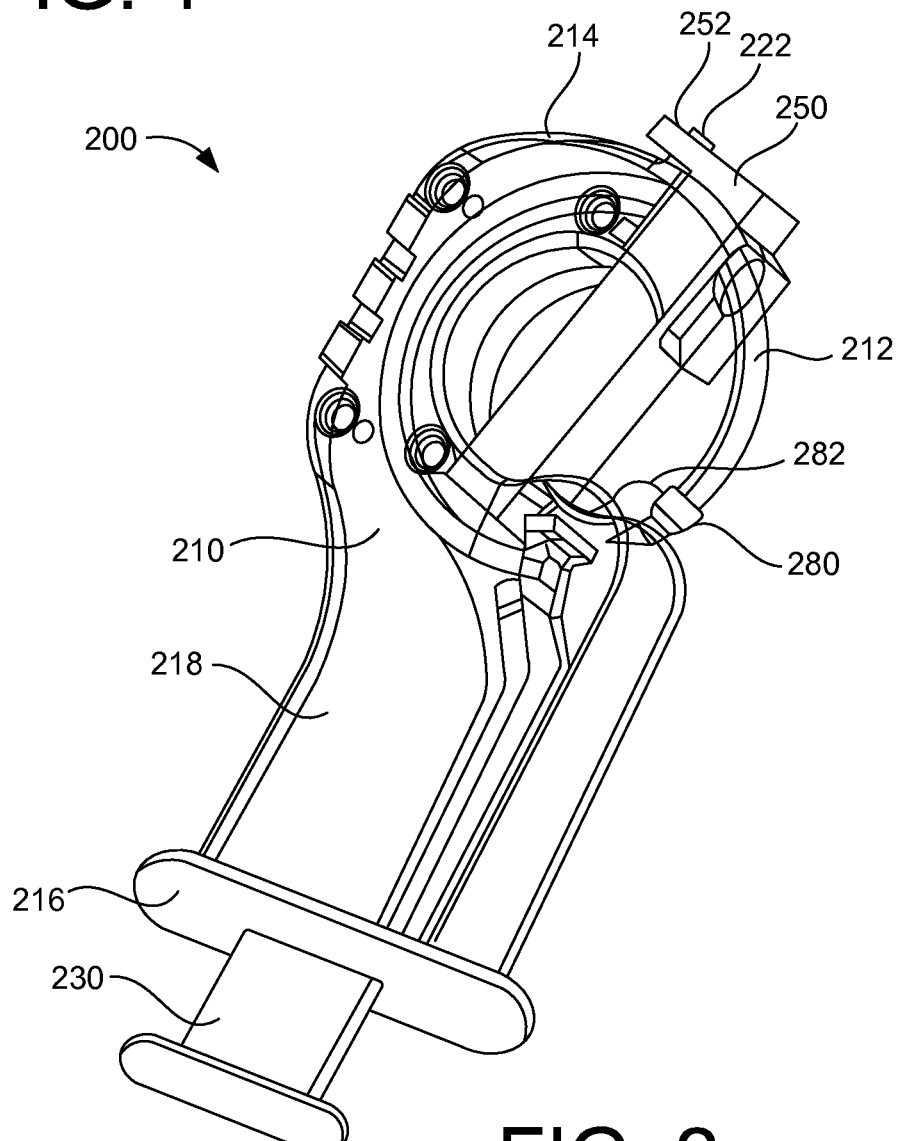
FIG. 2 is a perspective view of a medical device according to an embodiment of the invention.
Figure 3:
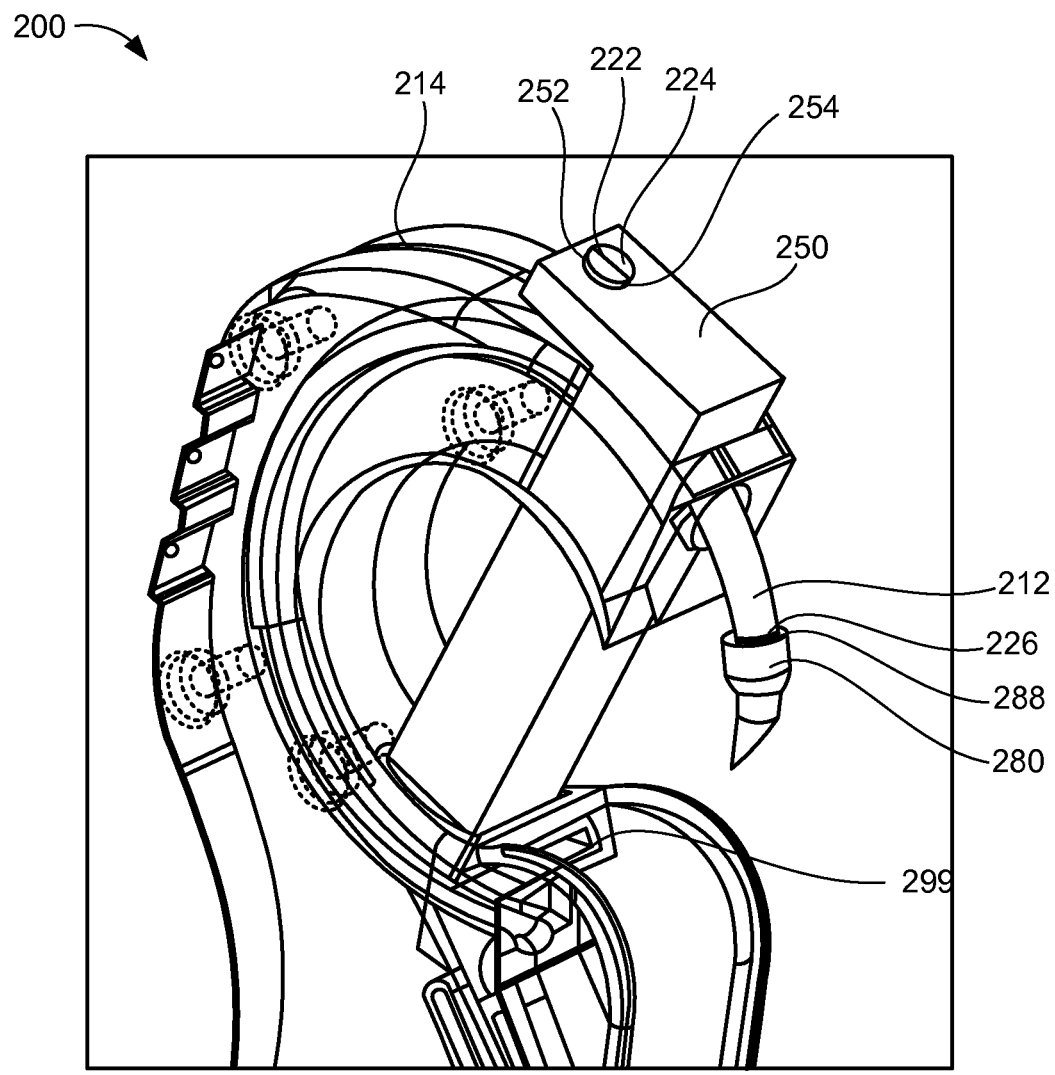
FIG. 3 is a perspective view of a distal portion of the medical device of FIG. 2.
Figure 4:
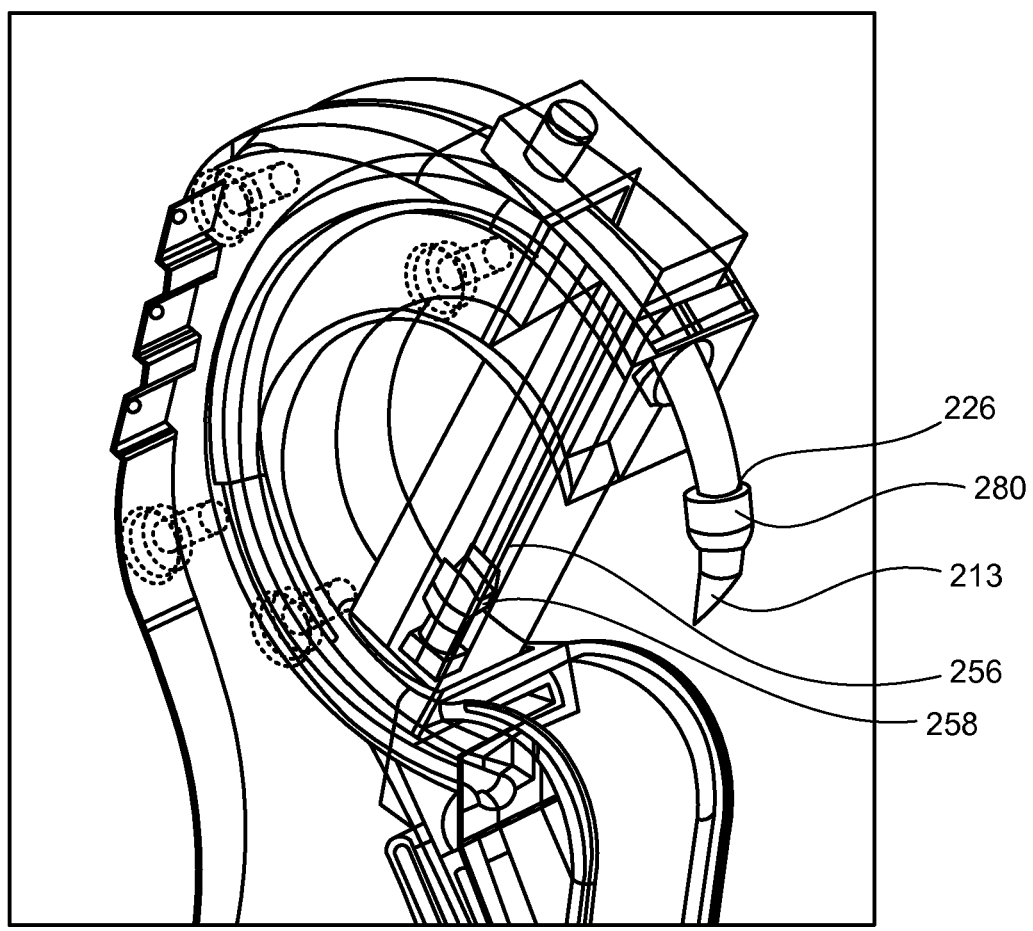
Figure 5:
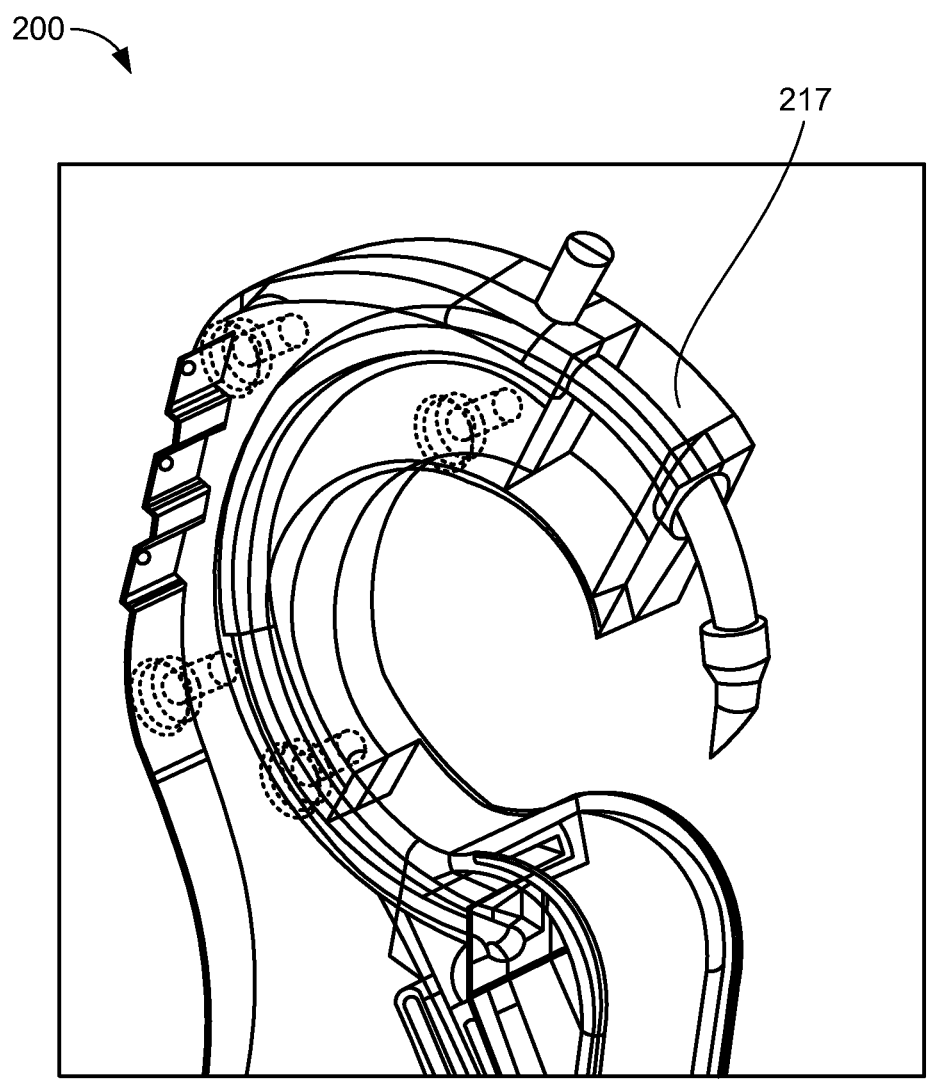
FIG. 5 is a perspective view of the distal portion of the medical device of FIG. 2.
Figure 6:
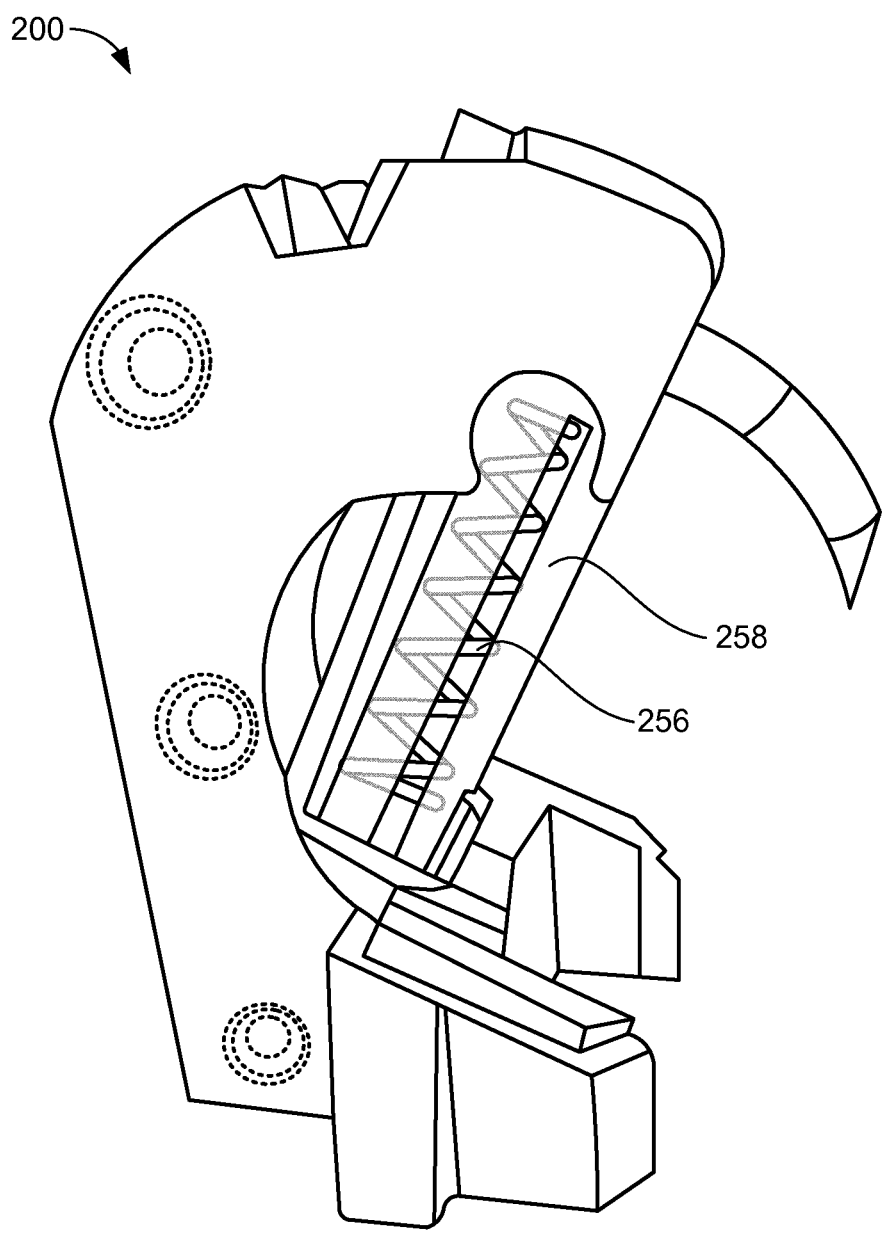
Figure 7:
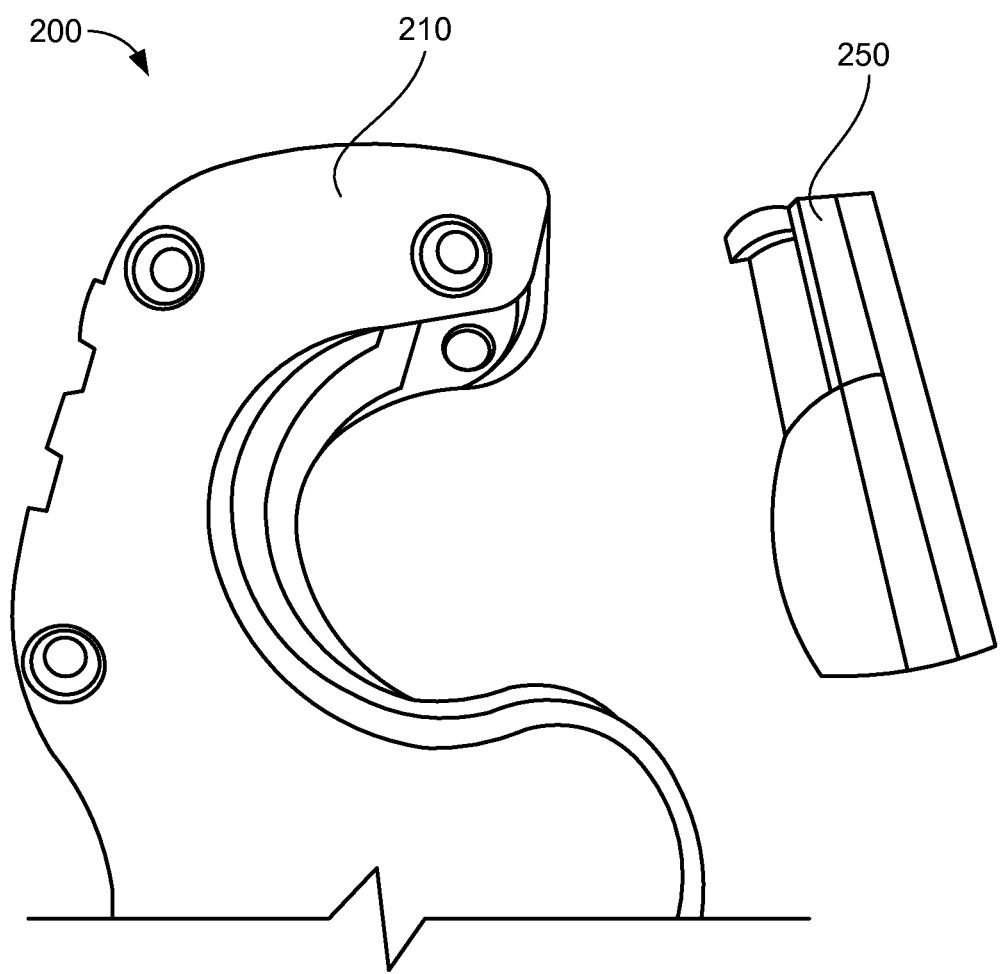
FIG. 7 is a perspective view of the distal portion of the medical device of FIG. 2.

FIGS. 2 to 7 illustrate a medical device 200 according to an embodiment of the invention. FIG. 2 is a perspective view of the medical device 200. FIG. 3 is a perspective view of a distal portion of the medical device 200. FIG. 4 is a perspective view of the distal portion of the medical device 200 with a portion of the device shown in see-through. FIG. 5 is a perspective view of the distal portion of the medical device 200. FIG. 6 is a perspective view of a distal portion of the medical device 200 with portions of the device shown in see-through. FIG. 7 is a perspective view of the distal portion of the medical device 200.

The medical device 200 includes a delivery tool 210 and a cartridge 250 coupled to the delivery tool 210. The delivery tool 210 has a distal end portion 214 and a proximal end portion 216. The delivery tool 210 includes a body portion or elongate portion 218 and a carrier member 212 that is movably coupled to a body portion 218 of the delivery tool 210. Specifically, the carrier member 212 may be moved from a first position (as illustrated, for example, in FIG. 7) with respect to the body portion 218 of the delivery tool 210 to a second position (as illustrated, for example, in FIG. 2) with respect to the body portion 218. The body portion 218 may be of any length or size. For example, it may be sufficiently long to allow a user to place the distal end portion 214 within a body of a patient and have the proximal end portion 216 extend from the body of the patient.

In some embodiments, the carrier member 212 may be placed or moved into more than two positions with respect to the body portion 218. For example, the carrier member 212 may be configured to be moved into three, four, five, or any other number of different positions with respect to the body portion 218.

The cartridge 250 is coupled to the delivery tool 210. In the illustrated embodiment, the cartridge 250 is removably coupled to the delivery tool 210. Accordingly, the cartridge 250 may be selectively coupled to (as illustrated, for example, in FIG. 2) or removed from (as illustrated, for example in FIG. 7) the delivery tool 210.

In the illustrated embodiment, the delivery tool 210 defines a receiving portion, such as a lumen or a slot, 217. The receiving portion 217 is configured to receive the cartridge 250. Additionally, the cartridge 250 includes a coupling member 252 that is configured to engage a coupling member 222 of the delivery tool 210 to help couple the cartridge 250 to the delivery tool 210 when the cartridge 250 is disposed within the receiving portion 217 of the delivery tool 210. Specifically, in the illustrated embodiment, the cartridge 250 includes or defines an opening 254 that engages or receives a post or projection 224 of the delivery tool 210 to help couple the cartridge 250 to the delivery tool 210 when the cartridge 250 is disposed within the receiving portion of the delivery tool 210.

The cartridge 250 is configured to retain an anchor or anchor member 280. For example, in some embodiments, the cartridge 250 defines a cavity 256 that is configured to receive, house, or retain the anchor 280. In the illustrated embodiment, the cartridge 250 is configured to retain more than one anchor or anchor member simultaneously. A spring or other biasing member 258 is disposed within the cavity 256 and is configured to help retain and advance the anchors or anchor members that are disposed within the cavity 254 of the cartridge 250.

Figure 19:
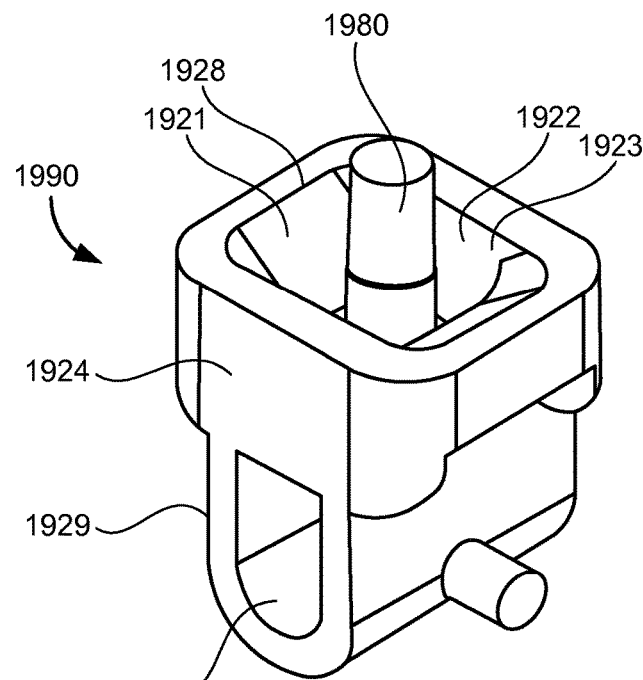
FIGS. 19 and 20 illustrate a catch according to an embodiment of the invention.
Figure 22:
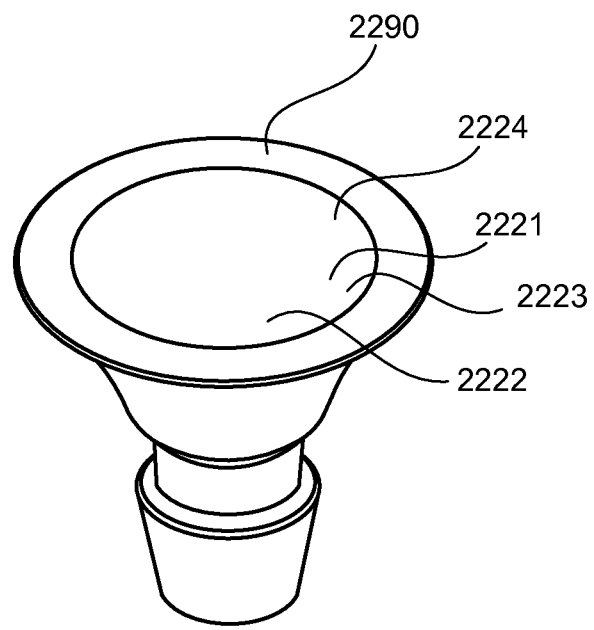

The medical device 200 includes a catch or catch member. The catch or catch member may be similar to catch 1990 (as shown in FIG. 19) or catch 2290 (as shown in FIG. 22). The catch may be removably coupled to the delivery tool 210. For example, the catch may be removably coupled to the delivery tool 210 at a nest area or location 299 (as shown in FIG. 3). In some embodiments, a series of catches (such as a series or a plurality of catches that are disposed within a cartridge) are removably coupled to the delivery tool 210 at a nest area or location 299. The catch or catch member is configured to be coupled to the anchor 280. For example, in some embodiments, the catch or catch member defines an opening or cavity and is configured to receive at least a portion of the anchor 280. In some embodiments, the catch 2290 is configured to be frictionally coupled to the anchor. In other embodiments, the catch may include a coupling member that is configured to engage a coupling member or coupling portion of the anchor to couple the catch to the anchor.

In the illustrated embodiment, the anchor 280 is attached to the catch via an attachment member 282. In some embodiments, the attachment member 282 is a filament, a suture, an elastic member or other type of line or structure that is configured to extend from the anchor 280 to the catch. In the illustrated embodiment, the attachment member 282 is a suture that has a first end portion 284 coupled to the anchor 280 and a second end portion coupled 286 to the catch.

The cartridge 250 allows the carrier 212 to access the anchor 280. For example, the cartridge 250 defines an opening or a lumen 260. The carrier 212 is configured to access the anchor 280 via the opening 260. For example, the carrier 212 is configured to extend into or through the opening 260 of the cartridge 250 to access or otherwise engage the anchor 280. In the illustrated embodiment, the anchor 280 defines a lumen 288. The carrier 212 is configured to extend into or through the opening 260 defined by the cartridge 250 and through the lumen 288 defined by the anchor 280.

In some embodiments, the carrier 212 is configured engage the anchor to move the anchor 280 out of or away from cartridge 250. For example, the carrier 212 is configured to move from a first or retracted position (as illustrated for example in FIG. 7) to a second or extended position (as illustrated, for example, in FIG. 2). The carrier 212 is configured to move the anchor 280 away from the cartridge when or as the carrier moves to its second or extended position or configuration. In the illustrated embodiment, the carrier 212 is configured to move the anchor 280 toward the catch as the carrier 212 moves from its first position to its second position. The carrier 212 is configured to move the anchor 280 away from the cartridge 250 and towards the catch such that the anchor 280 engages and is coupled to the catch.

In the illustrated embodiment, the carrier 212 includes or defines a shoulder or ridge 226. The shoulder or ridge 226 is configured to contact or engage the anchor to apply a force on the anchor to move the anchor as the carrier 212 is moved from its first position to its second position. The portion of the carrier 212 that is disposed distally of the shoulder or ridge 226 is sufficiently small to fit within or through the lumen 288 defined by the anchor 280. The shoulder or ridge 226 is sized such that it does not fit within the lumen 288 defined by the anchor 280. In illustrated embodiment, the carrier 212 includes a distal tip or end 213 that is sharp and is configured to pierce bodily tissue.

In the illustrated embodiment, the medical device 200 includes an actuator 230. The actuator 230 is operatively coupled to the carrier 212 and is configured to move the carrier 212 from its different positions. For example, in some embodiments, the actuator 230 can be moved in one direction to move the carrier 212 from its first position to its second position and may be moved in another direction to move the carrier from its second position to its first position. In some embodiments, the actuator 230 (and thus the carrier 212) is biased into one of its positions or directions.

In some embodiments, the medical device 200 may be inserted into the body of the patient such that the anchor 280 and the catch are disposed on opposite sides of bodily tissue (or such that some bodily tissue is disposed between the anchor 280 and the catch. In some embodiments, the device 200 may be used to secure or help secure an implant within a body of the patient. In some such embodiments, the medical device 200 may be inserted into a body of a patient such that bodily tissue and a portion of the implant are disposed between the anchor 280 and the catch.

The carrier 212 can then be moved from its first or retracted position to its second or extended configuration. As the carrier 212 is moved from its first position to its second position, the carrier 212 will engage the anchor 280, pass the anchor through the bodily tissue (and the implant) and into the catch such that the anchor 280 is coupled to the catch. The carrier 212 can then be retracted back to its first or retracted position, leaving the anchor 280 coupled to the catch. The catch can then be removed from the delivery tool 210 and the delivery tool 210 can be removed from the body of the patient thereby leaving the anchor 280 and the catch disposed within the body of the patient. In the illustrated embodiment, when the anchor 280 is passed through bodily tissue (and an implant) and is coupled to the catch (as described above), the catch, anchor 280, and attachment member 282 will collectively form a loop or circle about the tissue and implant to couple or help couple the implant to the bodily tissue.

The anchor or anchor member may be or any shape or size and may be formed of any biocompatible material. The anchor or anchor member is configured to be passed though bodily tissue and, in some embodiments, bodily implants.

FIGS. 8 to 13 are perspective views of various anchors according to embodiments of the invention.

Figure 8:
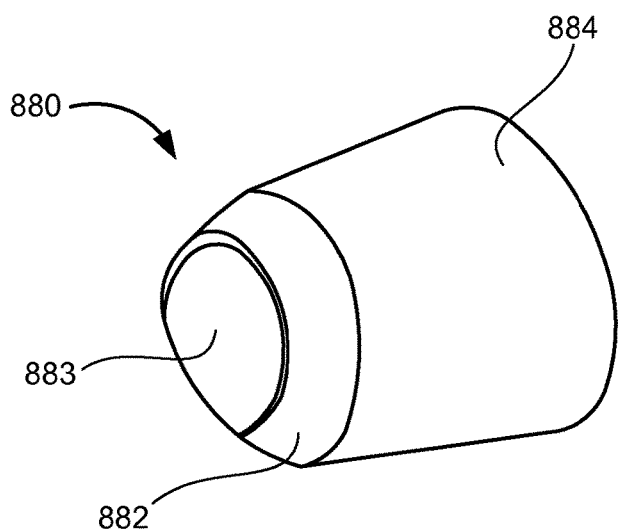
FIGS. 8 to 13 are perspective views of anchors according to embodiments of the invention.

FIG. 8 is a perspective view of anchor 880. The anchor 880 defines a lumen 883 that extends from one end portion 882 of the anchor 880 to another end portion 884 of the anchor 880. The lumen 883 is configured to receive a carrier or carrier member of a delivery tool. In some embodiments, the lumen 883 is configured to receive the carrier or carrier member of the delivery tool such that the carrier or carrier member extends through the lumen 883. The anchor 880 has a circular cross-section and includes a taper shape. Specifically, end portion 884 is larger than end portion 882.

Figure 9:
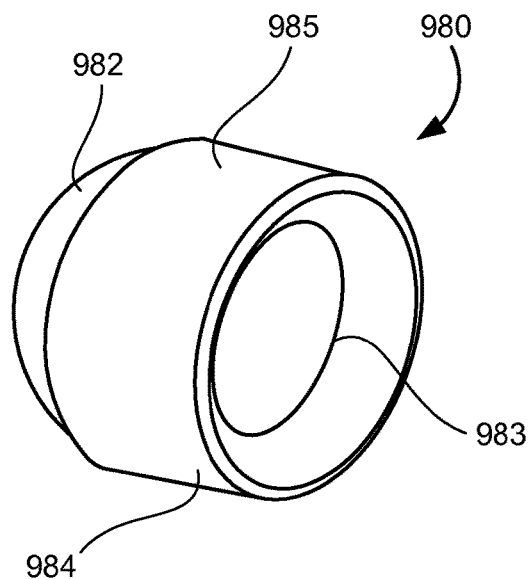

FIG. 9 is a perspective view of anchor 980. The anchor 980 defines a lumen 983 that extends from one end portion 982 of the anchor 980 to another end portion 984 of the anchor 980. The lumen 983 is configured to receive a carrier or carrier member of a delivery tool. In some embodiments, the lumen 983 is configured to receive the carrier or carrier member of the delivery tool such that the carrier or carrier member extends through the lumen 983. The anchor 980 has a circular cross-section and includes a step down or shoulder member 985. End portion 984 is larger than end portion 982.

Figure 10:
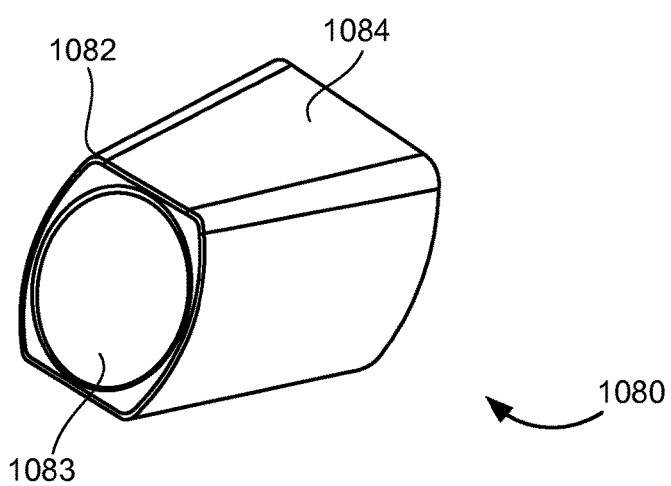

FIG. 10 is a perspective view of anchor 1080. The anchor 1080 defines a lumen 1083 that extends from one end portion 1082 of the anchor 1080 to another end portion 1084 of the anchor 1080. The lumen 1083 is configured to receive a carrier or carrier member of a delivery tool. In some embodiments, the lumen 1083 is configured to receive the carrier or carrier member of the delivery tool such that the carrier or carrier member extends through the lumen 1083. The anchor 1080 has a box or rectangular cross-section and includes a taper shape. Specifically, end portion 1084 is larger than end portion 1082.

Figure 11:
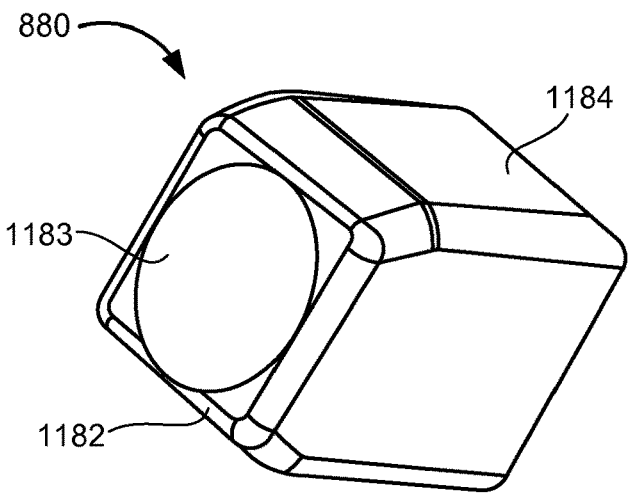

FIG. 11 is a perspective view of anchor 1180. The anchor 1180 defines a lumen 1183 that extends from one end portion 1182 of the anchor 1180 to another end portion 1184 of the anchor 1180. The lumen 1183 is configured to receive a carrier or carrier member of a delivery tool. In some embodiments, the lumen 1183 is configured to receive the carrier or carrier member of the delivery tool such that the carrier or carrier member extends through the lumen 1183. The anchor 1180 has a box or rectangular cross-section and includes a taper shaped portion 1187. Specifically, end portion 1184 is larger than end portion 1182.

Figure 12:
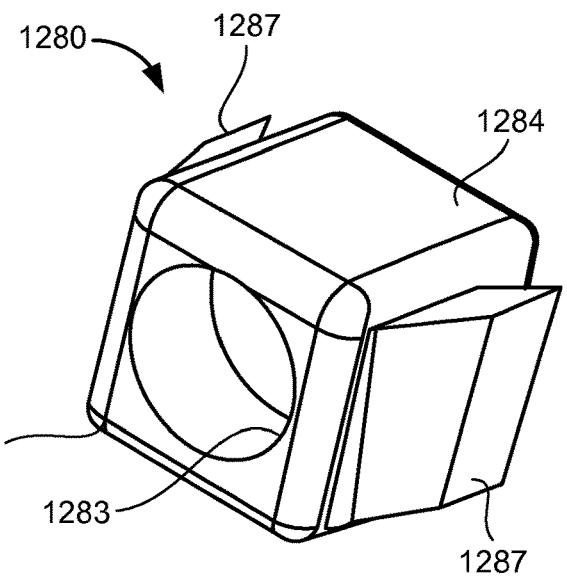

FIG. 12 is a perspective view of anchor 1280. The anchor 1280 defines a lumen 1283 that extends from one end portion 1282 of the anchor 1280 to another end portion 1284 of the anchor 1280. The lumen 1283 is configured to receive a carrier or carrier member of a delivery tool. In some embodiments, the lumen 1283 is configured to receive the carrier or carrier member of the delivery tool such that the carrier or carrier member extends through the lumen 1283. The anchor 1280 has a box or rectangular cross-section and includes projection members 1287. The projection members 1287 may be configured to help anchor or retain the anchor 1280 within bodily tissue or within a catch.

Figure 13:
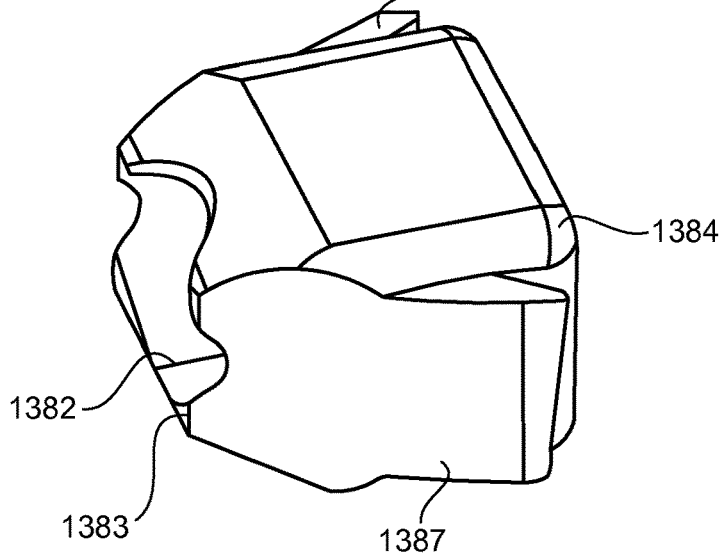

FIG. 13 is a perspective view of anchor 1380. The anchor 1380 defines a lumen 1383 that extends from one end portion 1382 of the anchor 1380 to another end portion 1384 of the anchor 1380. The lumen 1383 is configured to receive a carrier or carrier member of a delivery tool. In some embodiments, the lumen 1383 is configured to receive the carrier or carrier member of the delivery tool such that the carrier or carrier member extends through the lumen 1383. The anchor 1380 has a box or rectangular cross-section and includes projection members 1387. The projection members 1387 may be configured to help anchor or retain the anchor 1380 within bodily tissue or within a catch.

Figure 14:
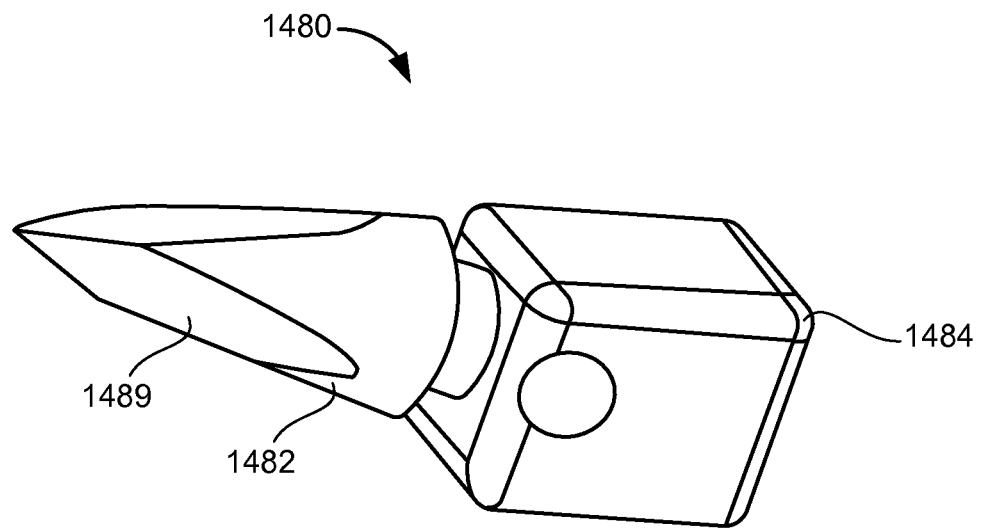
FIG. 14 is a perspective view of an anchor according to and embodiment of the invention.
Figure 15:
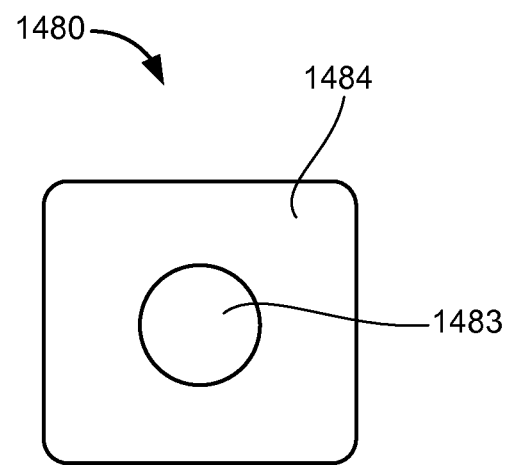
FIG. 15 is an end view of the anchor of FIG. 14.

FIG. 14 is a perspective view of an anchor 1480 according to an embodiment of the invention. FIG. 15 is an end view of the anchor 1480.

The anchor 1480 defines a cavity 1483. The cavity 1483 is configured to receive a carrier or carrier member of a delivery tool. In some embodiments, the cavity 1483 is configured to receive the carrier or carrier member of the delivery tool such that a portion of the carrier or carrier member is disposed within the cavity 1483. The anchor 1480 has a box or rectangular cross-section and includes a sharp or pointed portion 1489. The sharp or pointed portion 1489 may be configured to pierce or cut bodily tissue as the anchor 1480 is inserted into the body and passed through bodily tissue.

Figure 16:
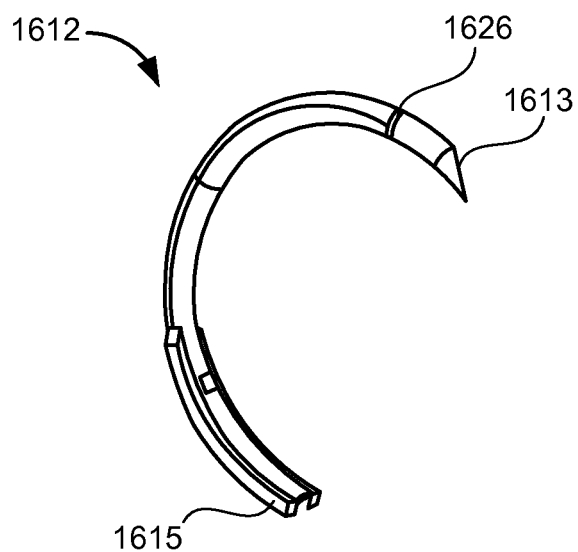
FIG. 16 is a perspective view of a carrier member of an embodiment of the invention.

FIG. 16 is a perspective view of a carrier 1612 according to an embodiment of the invention. The carrier 1612 may be used in conjunction with a medical device as described herein. In the illustrated embodiment, the carrier 1612 is curved or includes a curved portion. In other embodiments, the carrier can have any type of shape or curve. In some embodiments, the carrier 1612 is formed of a biocompatible material such as a metal or other material.

The carrier 1612 includes a distal tip 1613 that is sharp or pointed. The distal tip 1613 may be configured to pierce bodily tissue as the carrier 1612 is advanced through bodily tissue. In the illustrated embodiment, the distal tip 1613 is configured to be inserted into a lumen defined by an anchor (such as, for example, anchors 880, 980, 1080, 1180, 1280, and 1380). In some embodiments, the distal tip 1613 is configured to extend through the lumen defined by the anchor. The carrier includes a step-down or shoulder or ridge 1626. The shoulder or ridge 1626 is configured to contact or engage an end portion of the anchor to move the anchor or place a force on the anchor as the carrier 1612 is moved. The carrier 1612 includes a proximal end portion 1615 that is configured to be operatively coupled to an actuator (such as actuator 230) to facilitate the movement of the carrier 1612.

Figure 17:
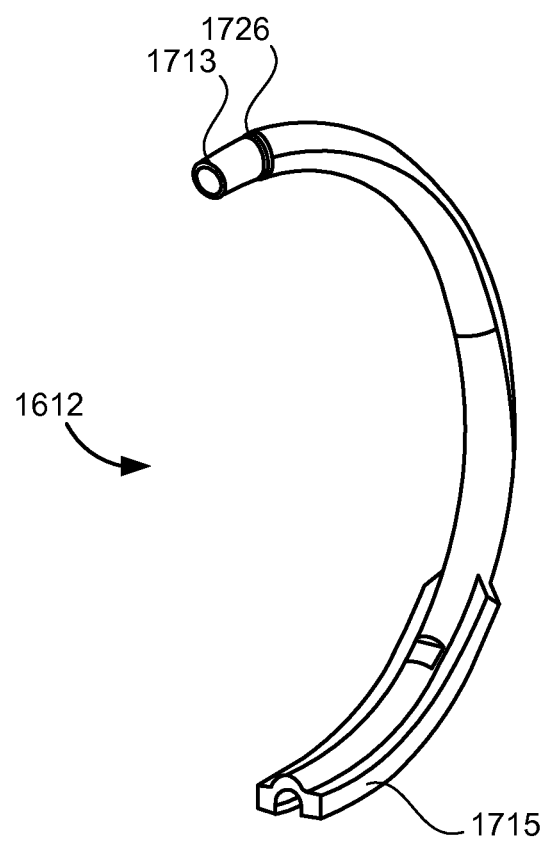
FIG. 17 is a perspective view of a carrier member of an embodiment of the invention.

FIG. 17 is a perspective view of a carrier 1712 according to an embodiment of the invention. The carrier 1712 may be used in conjunction with a medical device as described herein. In the illustrated embodiment, the carrier 1712 is curved or includes a curved portion. In other embodiments, the carrier can have any type of shape or curve. For example, in some embodiments, the carrier may be linear or substantially linear. In some embodiments, the carrier 1712 is formed of a biocompatible material such as a metal or other material.

The carrier 1712 includes a distal tip 1713 that is blunt or rounded. In the illustrated embodiment, the distal tip 1713 is configured to be inserted into a cavity or opening defined by an anchor (such as, for example, anchor 1480). The carrier includes a step-down or shoulder or ridge 1726. The shoulder or ridge 1726 is configured to contact or engage an end portion of the anchor to move the anchor or place a force on the anchor as the carrier 1712 is moved. The carrier 1712 includes a proximal end portion 1715 that is configured to be operatively coupled to an actuator (such as actuator 230) to facilitate the movement of the carrier 1712.

Figure 18:
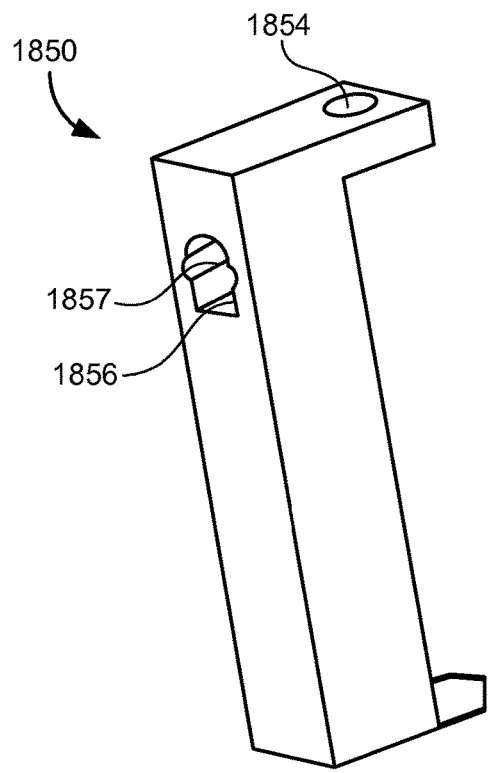
FIG. 18 is a perspective view of a cartridge according to an embodiment of the invention.

FIG. 18 is a perspective view of a cartridge 1850 according to an embodiment of the invention. The cartridge 1850 is configured to be coupled to a delivery tool and is configured to retain or house an anchor or a plurality of anchors. In the illustrated embodiment, the cartridge 1850 defines an opening 1854 that is configured to engage a portion of the delivery tool to help removably couple the cartridge to the delivery tool.

In the illustrated embodiment, the cartridge 1850 defines a lumen 1856 that is configured to retain our house the anchor or anchors. The cartridge 1850 also defines an opening 1857. The opening 1857 is in fluid communication with the lumen 1856 and is configured to allow the anchor to pass through. The cartridge 1850 also includes an opening on the opposite side of opening 1857 that is also in fluid communication with the lumen 1856. Accordingly, a carrier may be passed through the opening, engage an anchor, and move the anchor out of the lumen 1856 via the opening 1857. In some embodiments, the cartridge 1850 includes a spring or bias member disposed within the lumen 1856 and is configured to serially advance the anchors into a position proximate the opening 1857 (and in a position to be engaged by a carrier).

Figure 20:
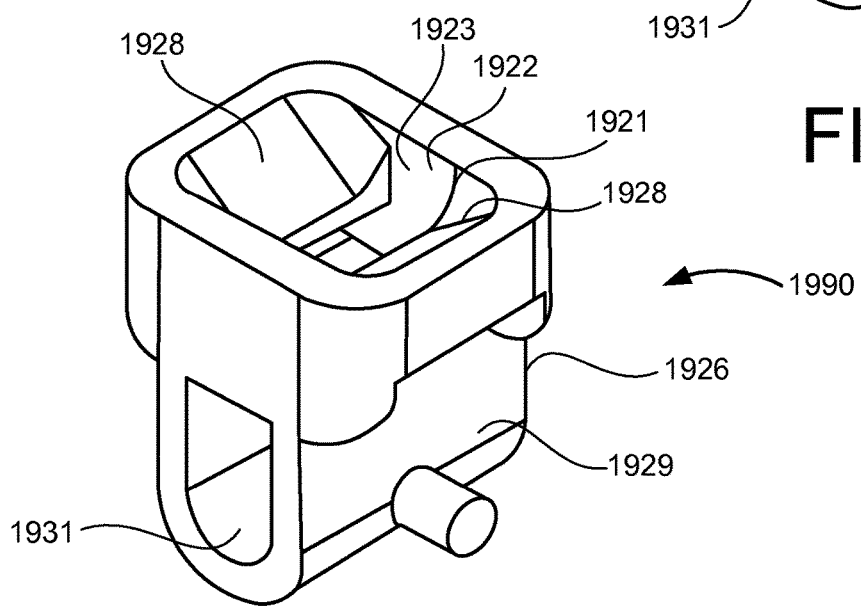

FIG. 20 is a perspective view of a catch 1990 according to an embodiment of the invention. FIG. 19 is a perspective view of the catch 1990 coupled to an anchor or a portion of an anchor 1980. The catch 1990 includes a receiving portion 1921. Specifically, the catch 1990 defines a cavity 1922 and an opening 1923 in communication with the cavity 1922. As best illustrated in FIG. 19, the receiving portion 1921 is configured to receive the anchor 1980 such that the anchor 1980 is received into the cavity 1922 through the opening 1923.

In the illustrated embodiment, the catch 1990 includes a sidewall 1924 that defines the cavity 1922. The catch 1990 also includes projection members or flaps 1928 that extend from the sidewall 1924 into the cavity 1922. The projection members or flaps 1928 are configured to flex or bend when the anchor 1980 is inserted into the cavity 1922 via the opening 1923. As the projection members or flaps 1928 flex or bend the anchor 1980 can be more fully received or inserted into the cavity 1922. In some embodiments, the anchor 1980 includes an extended portion, a projection or rib. Once the rib or extended portion of the needle passes the projection members or flaps 1928 (while the projection members or flaps 1928 are in their flexed or bent configuration), the projection members 1928 will return to their unflexed configuration thereby capturing the anchor within the cavity or coupling the anchor 1980 to the catch 1990 (as best illustrated in FIG. 19). Accordingly, the anchor 1980 is configured to be moved into the catch 1990 in one direction, but is retained within the cavity 1922 and prevented from moving in an opposite direction.

In the illustrated embodiment, the anchor 1980 includes a tissue piercing portion. As best illustrated in FIG. 19, the catch 1990 is configured to couple to the anchor 1980 such that the tissue piercing portion of the anchor 1980 is disposed within the cavity 1922 defined by the catch 1990. In other words, the distal end portion or the tissue piercing portion of the anchor 1980 does not extend from the catch 1990.

In the illustrated embodiment, the catch 1990 includes a base portion 1926. The base portion 1926 includes a U-shaped member 1929. The base portion 1926 of the catch 1990 provides a surface 1931 to contact or otherwise help prevent the tissue piercing portion of the anchor 1980 from being over inserted into the catch 1990 or from extending from the catch 1990.

In some embodiments, the projection members 1928 are configured to help facilitate the guiding of the anchor 1980 into the cavity 1922 of the catch 1990. Specifically, in the illustrated embodiment, the projection members 1928 are sloped or angled. As the anchor 1980 enters the cavity 1922 and the anchor 1980 contacts the projection members 1928, the anchor 1980 will be guided or forced towards the center of the cavity 1922.

Figure 21:
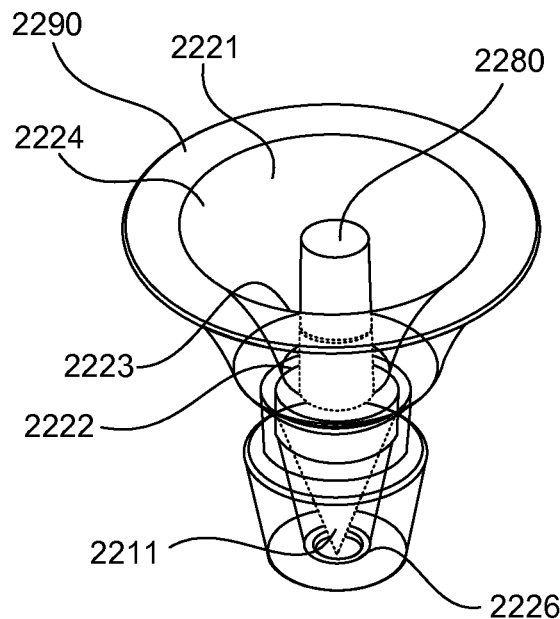
FIGS. 21 and 22 illustrate a catch according to an embodiment of the invention.

FIG. 22 is a perspective view of a catch 2290 according to an embodiment of the invention. FIG. 21 is a see-though view of the catch 2290 coupled to an anchor or a portion of an anchor 2280. The catch 2290 includes a receiving portion 2221. Specifically, the catch 2290 defines a cavity 2222 and an opening 2223 in communication with the cavity 2222. As best illustrated in FIG. 19, the receiving portion 2221 is configured to receive the anchor 2280 such that the anchor 2280 is received into the cavity 2222 through the opening 2223.

In the illustrated embodiment, the catch 2290 includes a sidewall 2224 that defines the cavity 2222. The sidewall 2224 defines a conical or funnel type or shaped cavity. In some embodiments, the sidewall 2224 is configured to contact the anchor 2280 to frictionally couple the anchor 2280 to the catch 220. Accordingly, the anchor 2280 is configured to be moved into the catch in one direction, but is retained within the cavity 2222 and prevented from moving in an opposite direction. In the illustrated embodiment, the sidewall 2224 includes a projection or a rib 2225 that is configured engage the anchor 2280 to help couple the anchor 2280 to the catch 2290. In some embodiments, the sidewall includes a plurality of projections or ribs.

In the illustrated embodiment, the anchor 2280 includes a tissue piercing portion 2211. As best illustrated in FIG. 21, the catch 2290 is configured to couple to the anchor 2280 such that the tissue piercing portion 2211 of the anchor 2280 is disposed within the cavity 2222 defined by the catch 2290. In other words, the distal end portion or the tissue piercing portion 2211 of the anchor does not extend from the catch 2290.

In the illustrated embodiment, the catch 2290 includes a base portion 2226. The base portion 2226 of the catch 2290 provides a surface to contact or otherwise prevent the tissue piercing portion 2211 of the anchor 2280 from extending from the catch 2290.

In the illustrated embodiment, the funnel shape or the funnel like shape of the catch 2290 (or the sidewall 2224 of the catch) help facilitate the guiding of the anchor 2280 into the cavity 2222 of the catch 2290. Specifically, as the anchor 2280 enters the cavity 2222, if the anchor 2280 happens to contact the sidewall 2224, the anchor 2280 will be guided or forced towards the center of the cavity 2222.

Figure 23:
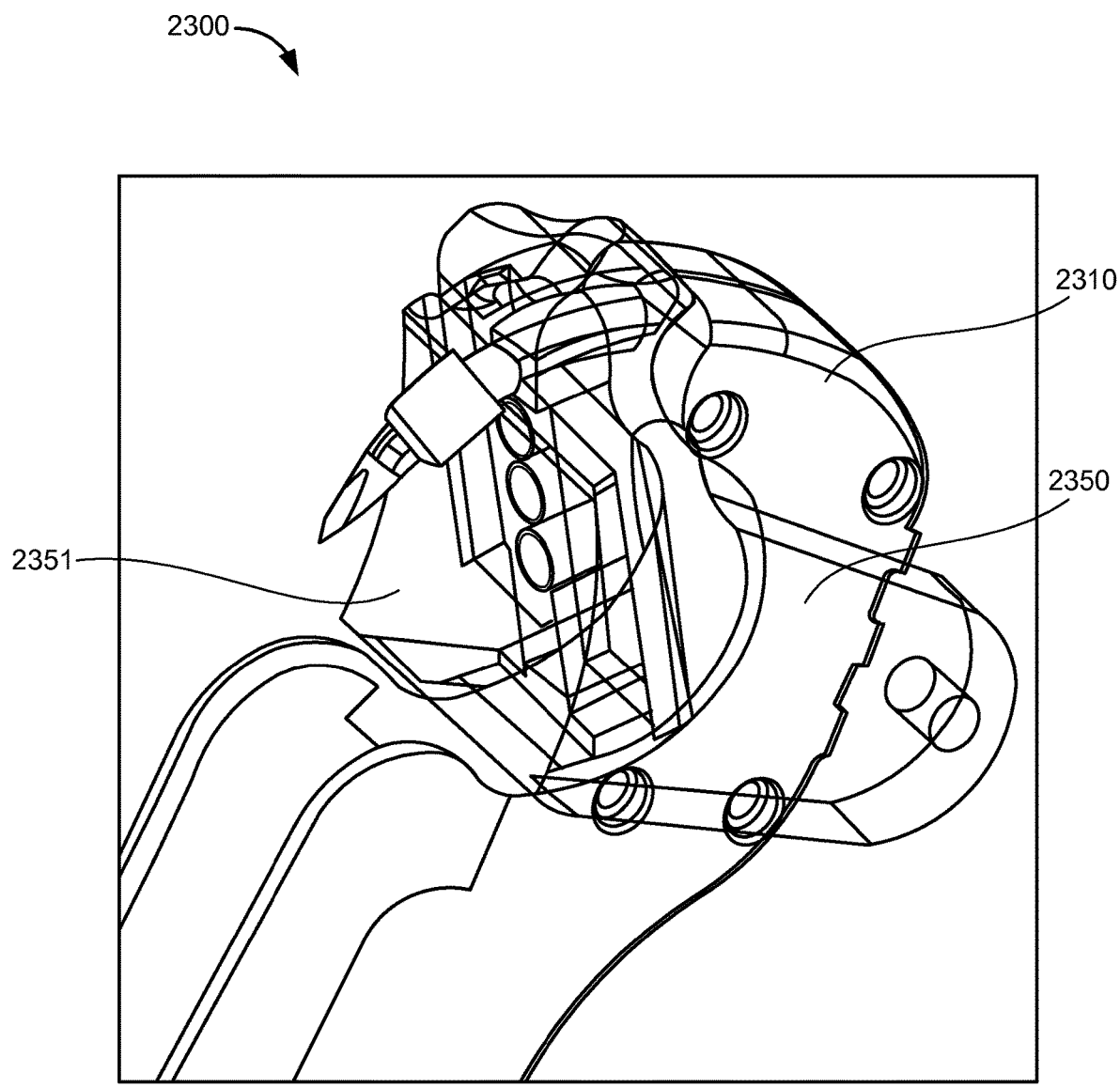
FIGS. 23 to 25 illustrate a medical device according to an embodiment of the invention.
Figure 24:
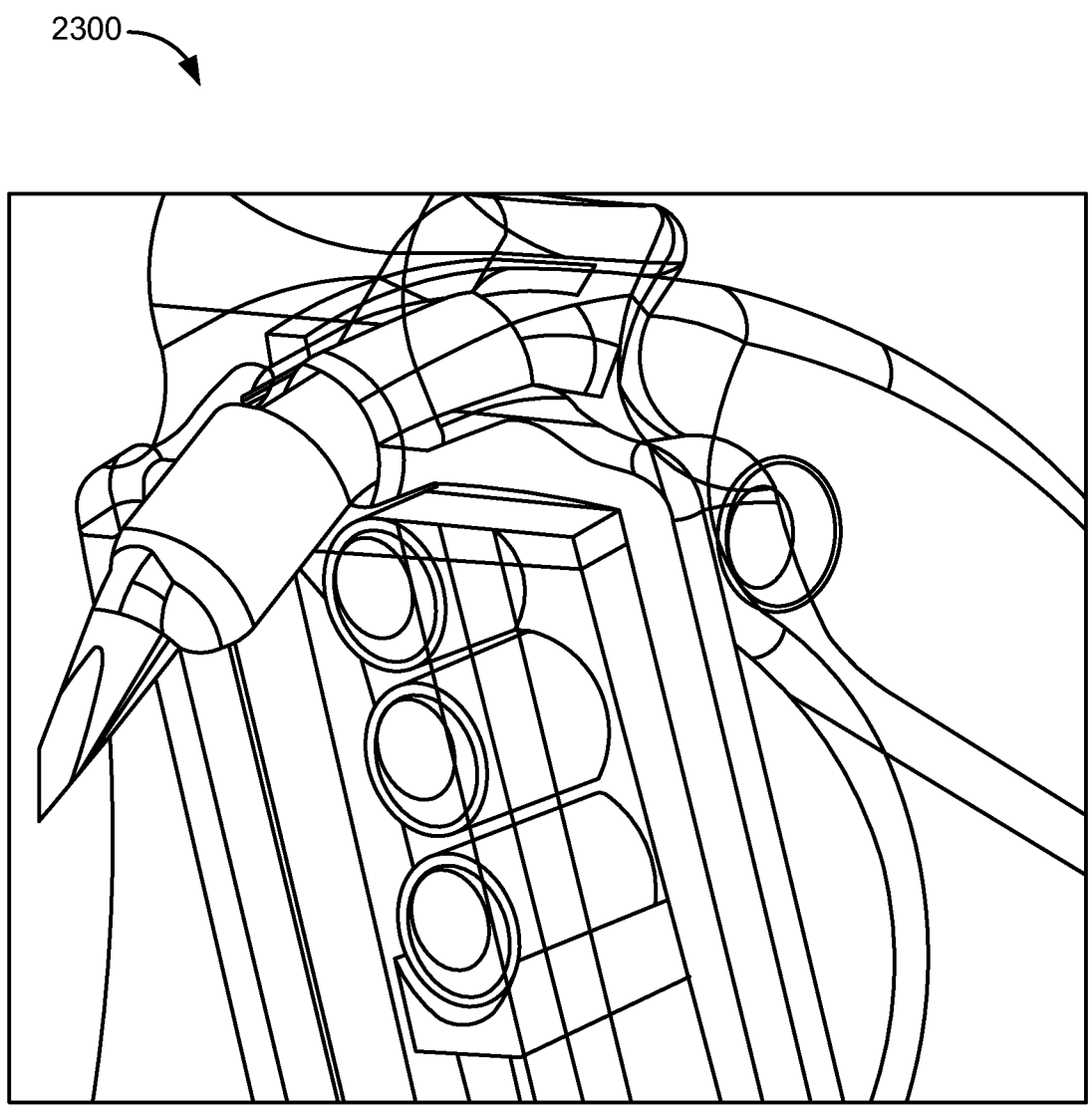
Figure 25:
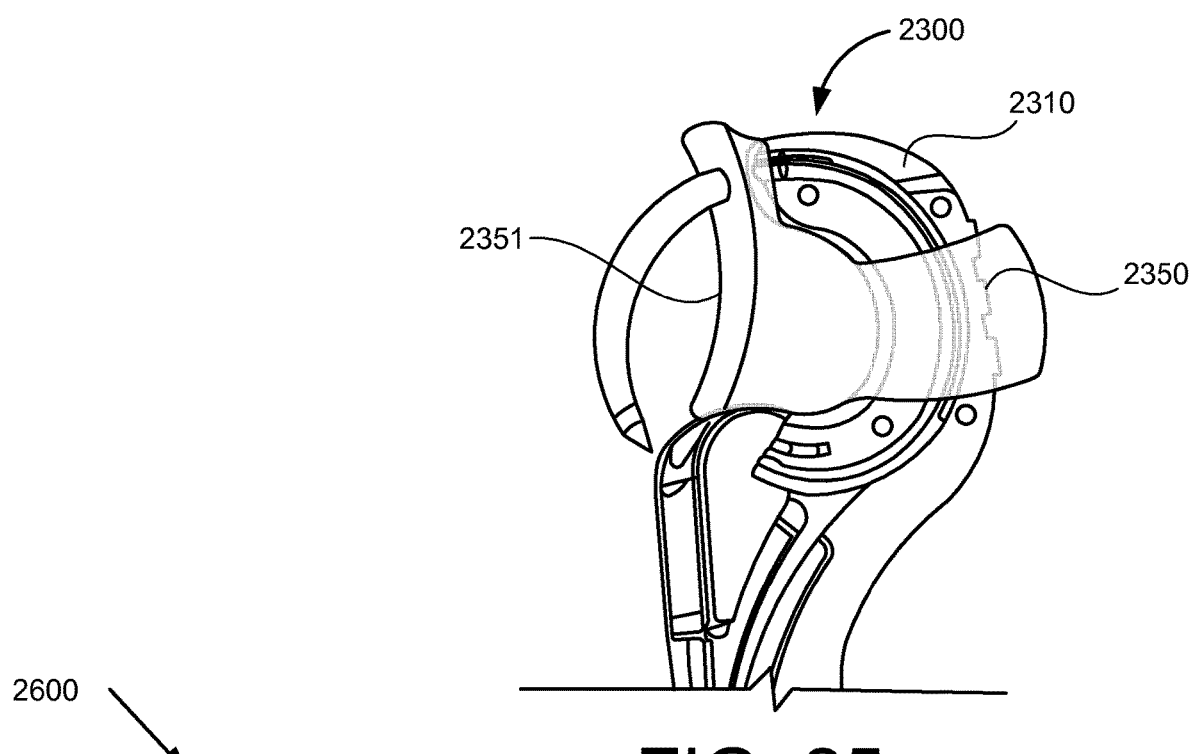

FIGS. 23 to 25 illustrate a medical device 2300 according to an embodiment of the invention. In the illustrated embodiment, the device 2300 includes a cartridge 2350 that snap-fits around a back side of the delivery tool 2310. The cartridge 2350 includes a front side or face 2351 that is configured to contact bodily tissue so as to serve as a depth control so as to not allow the carrier or anchor to be over inserted into bodily tissue.

Figure 26:
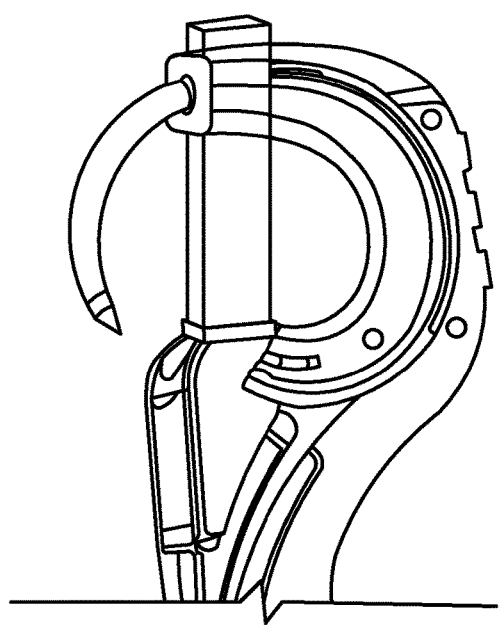
FIGS. 26 and 27 illustrate a medical device according to an embodiment of the invention.
Figure 27:
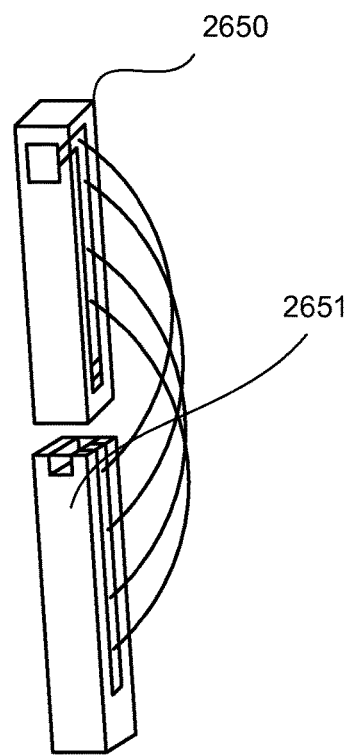

FIGS. 26 and 27 illustrate a medical device 2600 according to an embodiment of the invention. The device 2600 houses a plurality anchors and a plurality of catches. Specifically, as illustrated in FIG. 27, a cartridge 2650 may house the plurality of anchors and another cartridge 2651 may house the catches. The cartridges 2650 and 2651 may be movably coupled to or fixedly coupled to the device 2600. Each of the plurality of anchors may be coupled (such as via a suture or an coupling member) to one of the catches. In some embodiments, the cartridges 2650 and the 2651 may house biasing members, such as springs, that are configured to move the anchors and catches into place within the cartridges 2650 and 2651.

Figure 28:
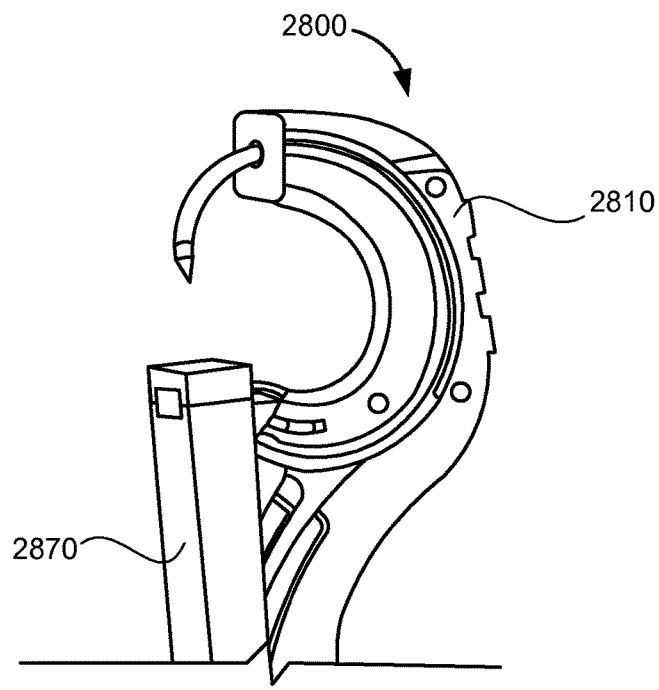
FIGS. 28 and 29 illustrate a medical device according to an embodiment of the invention.
Figure 29:
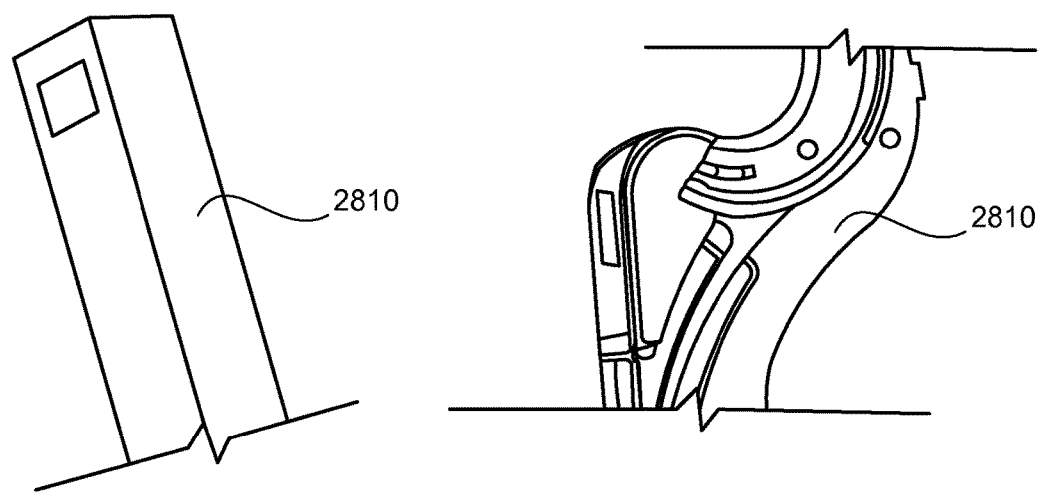

FIGS. 28 and 29 illustrate a medical device 2800 that includes a cartridge 2870 that is configured to house or retain a catch or a plurality of catches. In some embodiments, the carrier 2870 is removably coupled to the delivery tool 2810. For example, in some embodiments, the cartridge 2870 includes a snap portion or member that is configured to engage a portion of the delivery tool 2810 to snap fit the cartridge 2870 to the delivery tool 2810.

Figure 30:
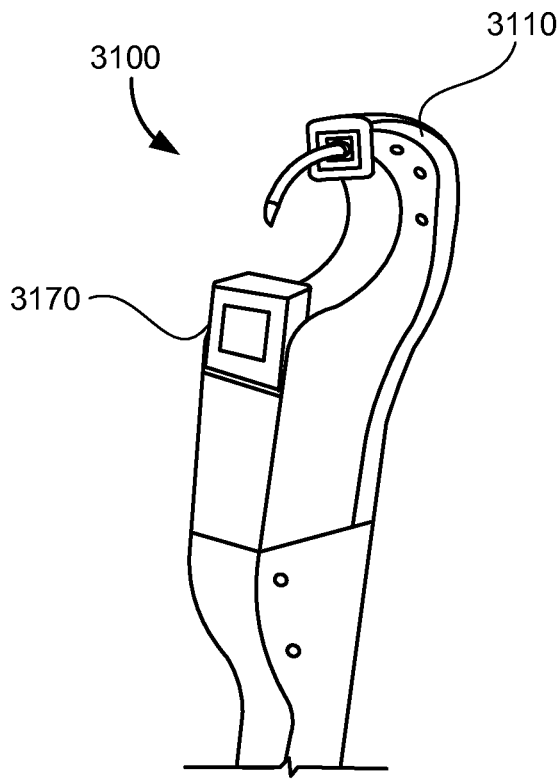
FIGS. 30 and 31 illustrate a medical device according to an embodiment of the invention.
Figure 31:
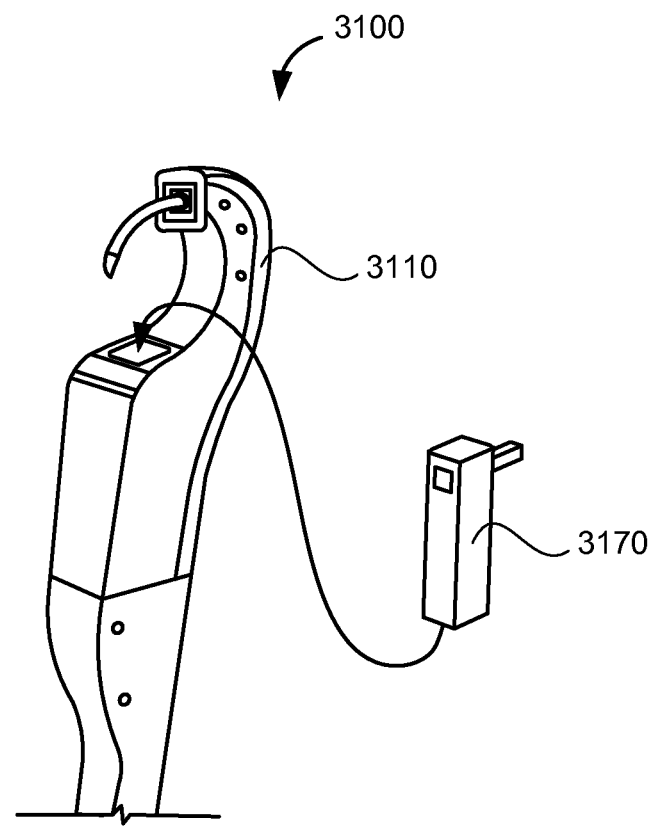

FIGS. 30 and 31 illustrate a medical device 3100 that includes a cartridge 3170 that is configured to house or retain a catch or a plurality of catches. In some embodiments, the cartridge 3170 is removably coupled to the delivery tool 3110. For example, in some embodiments, the cartridge 3170 is slidably coupled to the delivery tool 3110 such as into a cavity defined by the delivery tool 3110.

Figure 32:
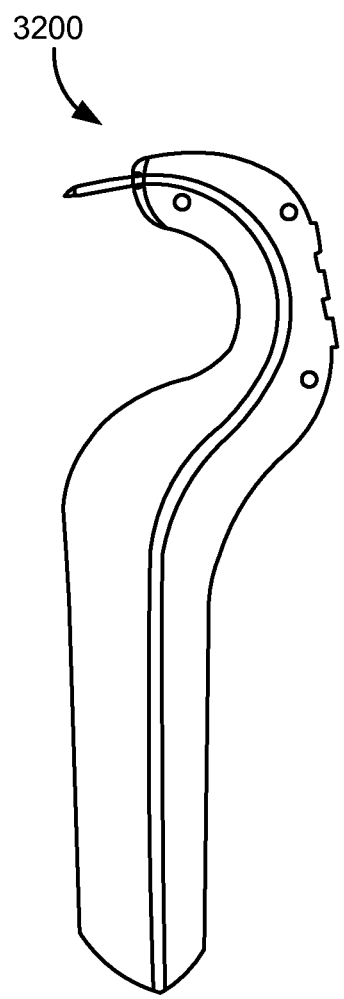
FIGS. 32 and 33 illustrate a medical device according to an embodiment of the invention.
Figure 33:
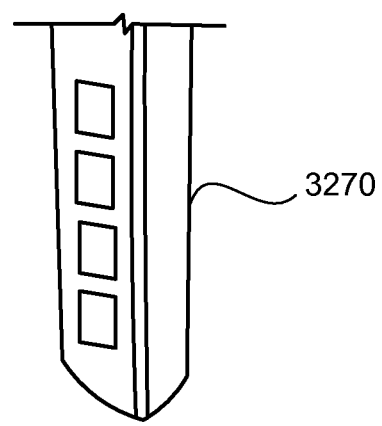

FIGS. 32 and 33 illustrate a medical device 3200. The device 3200 includes a cartridge 3270 that is configured to house or retain a catch or a plurality of catches. The cartridge 3270 includes a spring, a nitinol wire, or another biasing member to move the catches into position.

FIGS. 34 and 35 illustrate a cam or track system 3405 that is configured to move the catches into position each time the actuator is actuated. FIG. 36 illustrates a path 3406 that a cam may move to contact and move the catches. In some embodiments, the system 3405 includes a wire 3407, such as a nitinol wire, and a pusher 3409 to contact and move the catches.

In some embodiments, the device includes a cover or shield that is configured to cover or surround the catches or the anchors. For example, the covers or shields may be used to cover or surround the catches and the anchors while the device is placed or moved within the body of the patient.

FIG. 36 is a series of stacked catches 3690 as they would be stacked in a cartridge. In the illustrated embodiment, the catches 3690 define an opening 3691 on an angled surface so that the openings 3691 may be accessed (such as by a carrier and/or an anchor) while the catches are in a stacked relationship. In some embodiments, the catches may contain a breakable portion that is configured to break or release when the anchor or carrier contacts the catch.

Figure 37:
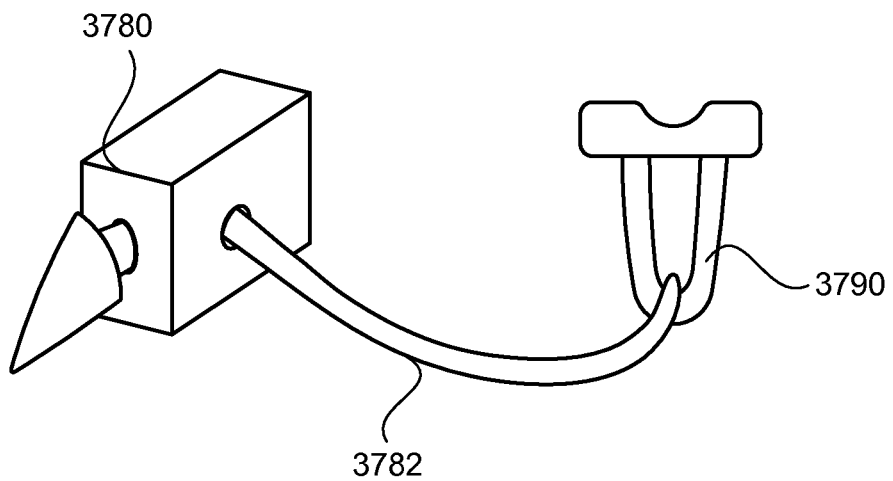
FIG. 37 is a perspective view of an anchor, coupling member, and a catch according to an embodiment of the invention.

FIG. 37 is a perspective view of an anchor member 3780, a coupling member 3782, and a catch 3790. The anchor 3780 may be formed of any type of material such as a polymer material or a metal material. In some embodiments, the anchor 3780 is made from or formed of a bioabsorbable material. In other embodiments, the anchor 3780 is made from or formed of a non-bioabsorbable material.

The coupling member 3782 is coupled to the anchor or anchor member 3780. In some embodiments, the coupling member 3782 is a suture. In some embodiments, the coupling member 3782 is coupled to the anchor 3780 by melting or welding the materials together. In other embodiments, another coupling mechanism, such as an adhesive, is used to couple the coupling member 3782 to the anchor 3780. In some embodiments, the anchor 3780 and the coupling member are formed as one piece, for example through a molding process.

In the illustrated embodiment, the coupling member 3782 is also coupled to the catch 3790. In some embodiments, the coupling member 3782 is mechanically coupled to the catch 3790. For example, the coupling member 3782 may be tied or frictionally coupled to the catch 3790.

Figure 38:
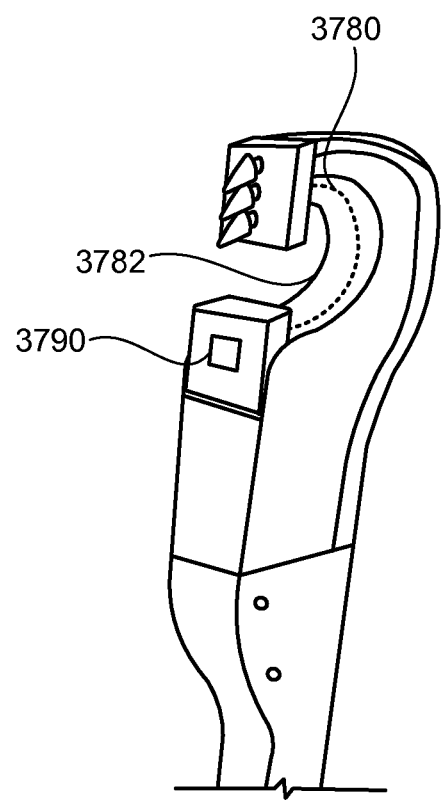
FIG. 38 is a perspective view of a distal end portion of a delivery tool according to an embodiment of the invention.

FIG. 38 illustrates the anchor 3780, the coupling member 3782, and the catch 3790 loaded on a delivery tool for placement within a body of a patient. As described above, a carrier or carrier member of the delivery tool may engage the anchor 3780 and move the anchor 3780 towards the catch 3790. The anchor 3780 is then received by and coupled to the catch 3790.

Figure 39:
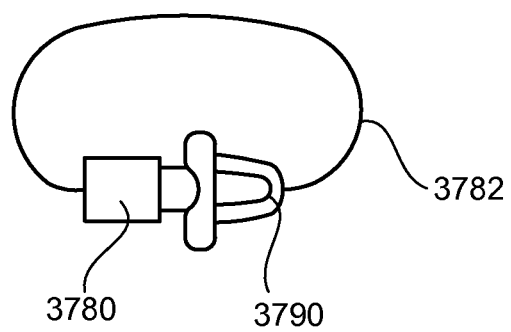
FIG. 39 is a perspective view of the anchor of FIG. 37 coupled to the catch of FIG. 37 according to an embodiment of the invention.

As illustrated in FIG. 39, when the anchor 3780 is coupled to the catch 3790 the anchor 3780, the coupling member 3782, and the catch 3790 collectively form a loop or circle. In some embodiments, when placed within the body, the loop or circle formed by the anchor 3780, the coupling member 3782, and the catch 3790 extend through bodily tissue and a bodily implant to couple the bodily implant to the bodily tissue. In some embodiments, the coupling of the coupling member 3782 to the catch 3790 may be adjusted (retied or cinched) so as to make the loop formed smaller and more tightly couple the bodily implant to the bodily tissue.

Figure 40:
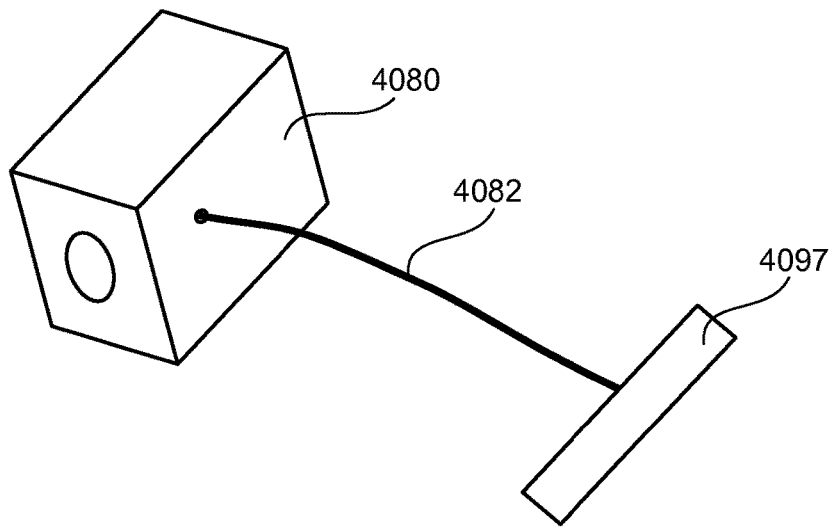
FIGS. 40 and 41 are perspective views of anchor devices according to embodiments of the invention.

FIG. 40 is a perspective view of an anchor 4080, a coupling member 4082, and a T shaped anchor 4097. One end portion of the coupling member 4082 is coupled to the anchor 4080 and another end portion of the coupling member 4082 is coupled to the T shaped anchor 4097. In other embodiments, the second end portion of the coupling member 4082 is coupled to an anchor that has a shape other than a T shape.

Figure 41:
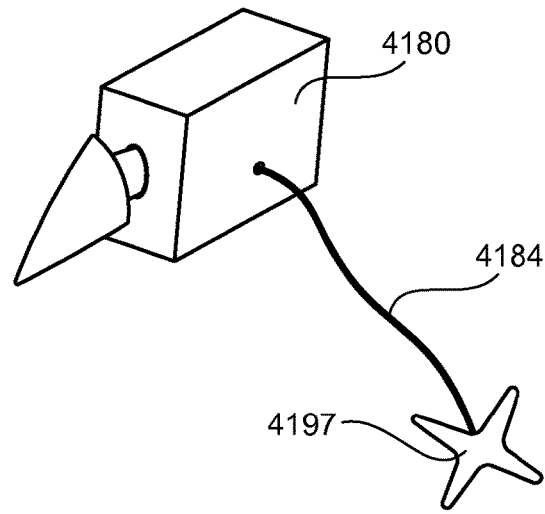

FIG. 41 is a perspective view of an anchor 4180, a coupling member 4182, and an X shaped anchor 4197. One end portion of the coupling member 4182 is coupled to the anchor 4180 and another end portion of the coupling member 4182 is coupled to the X shaped anchor 4197. In other embodiments, the second end portion of the coupling member 4182 is coupled to an anchor that has a shape other than an X shape. For example, the second end portion of the coupling member 4182 may be coupled to any shaped member, such as any three dimensional shaped member. In some embodiments, the x shaped member (or member of another shape) is configured to help prevent the coupling member from being pulled from bodily tissue or otherwise passed through too much bodily tissue.

Figure 42:
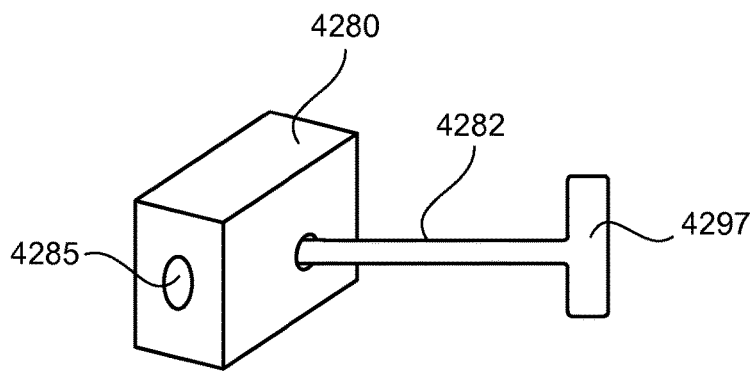
FIG. 42 is a perspective view of an anchor mechanism according to an embodiment of the invention.

FIG. 42 is a perspective view of an anchor 4280, a coupling member 4282, and a T shaped anchor 4297. In the illustrated embodiment, the coupling member 4282 is unitarily or monolithically formed with the anchor 4280 and the T shaped anchor 4297. While the T shaped anchor is illustrated as having a T shaped, the shaped anchor can be of any shape.

Figure 43:
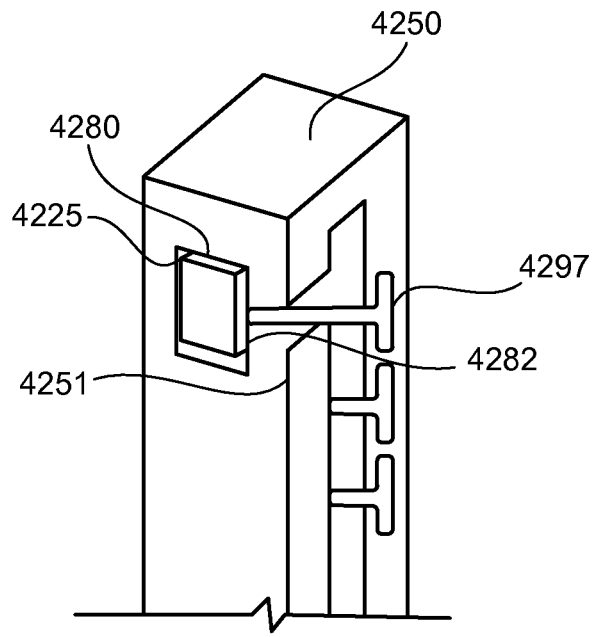
FIG. 43 is a perspective view of the anchor mechanism of FIG. 42 disposed within a cartridge according to an embodiment of the invention.

FIG. 43 is a perspective view of the anchor 4280, the coupling member 4282, and the T shaped anchor 4297 disposed within a cartridge 4250. The cartridge 4250 may be coupled to and used with a delivery tool as described above. The cartridge 4250 is configured to retain or house the anchor 4280 (and in the illustrated embodiment, is configured to retain or house a plurality of the anchors 4280). The cartridge 4250 defines a slot 4251. The coupling member 4282 extend from the slot 4251. In other embodiments, the cartridge 4250 includes a secondary housing portion that is configured to receive and house the coupling member 4282 and the T shaped anchor 4297. In use, the cartridge 4250 may be coupled to a delivery tool and a carrier of the delivery tool may engage the anchor 4280 (for example by extending through the lumen 4285 defined by the anchor 4280) and move the anchor 4280 out of or away from the cartridge 4250 (such as through opening 4253 of the cartridge 4250). In some embodiments, the cartridge includes a biasing member such as a spring that is configured to move the next anchor in place within the cartridge 4250 for engagement with the carrier.

Figure 44:
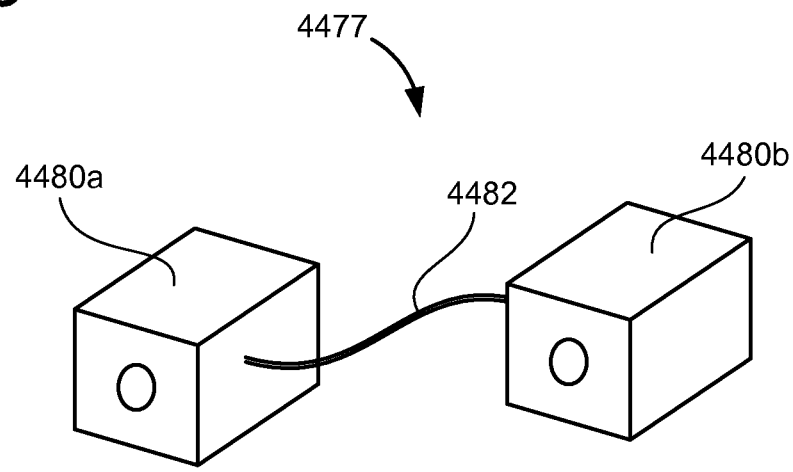
FIG. 44 is a perspective view of an anchor mechanism according to an embodiment of the invention.

FIG. 44 is a perspective view of an anchor mechanism 4477. The anchor mechanism 4477 includes a first anchor 4480*a* and a second anchor 4480*b*. The first anchor 4480*a* is coupled to the second anchor 4480*b* via a coupling member 4482. In some embodiments, the coupling member 4482 is fixedly coupled to each of the first anchor 4480*a* and the second anchor 4480*b*. For example, the coupling member may be molded or welded to the anchors. In other embodiments, the coupling member may be mechanically coupled to the one of the anchors. For example, the coupling member may be tied to or frictionally coupled to one of the anchors. In such embodiments, the length of the coupling member may be adjustable (and the anchors may be cinched together).

Figure 45:
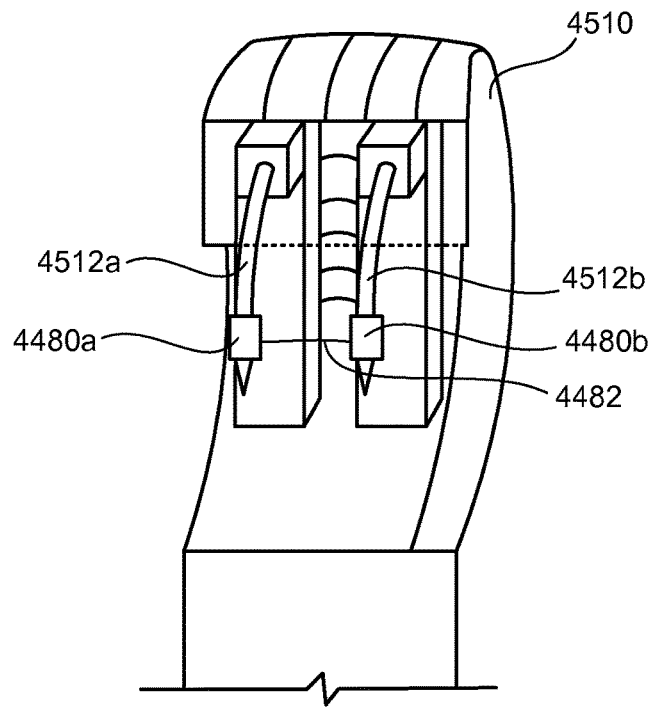
FIG. 45 is a perspective view of a distal end portion of a delivery tool according to an embodiment of the invention.

FIG. 45 is a perspective view of a delivery tool 4510 in accordance with the invention. The delivery tool 4510 is configured to place the anchor mechanism 4477 within a body of a patient. The delivery tool 4510 includes a first carrier 4512*a* and a second carrier 4512*b*. The carriers 4512*a* and 4512*b* are configured to engage the anchors 4480*a* and 4480*b* and move the anchors into bodily tissue. In some embodiments, the carriers 4512*a* and 4512*b* are operatively coupled to a single actuator so that the carriers 4512*a* and 4512*b* are moved simultaneously. In other embodiments, the carriers 4512*a* and 4512*b* are operatively coupled to separate actuators.

Figure 46:
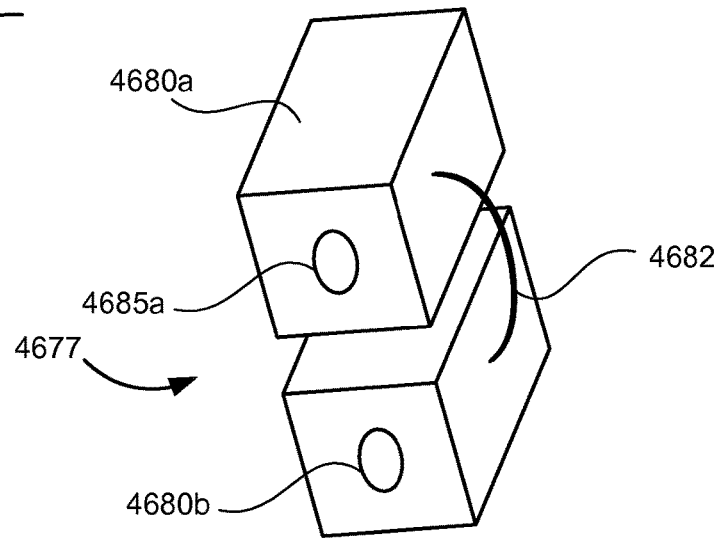
FIG. 46 is a perspective view of an anchor mechanism according to an embodiment of the invention.

FIG. 46 is a perspective view of an anchor mechanism 4677. The anchor mechanism 4677 includes a first anchor 4680*a* and a second anchor 4680*b*. The first anchor 4680*a* is coupled to the second anchor 4680*b* via a coupling member 4682. In some embodiments, the coupling member 4682 is fixedly coupled to each of the first anchor 4680*a* and the second anchor 4680*b*. For example the coupling member may be molded, glued, or welded to the anchors.

Figure 47:
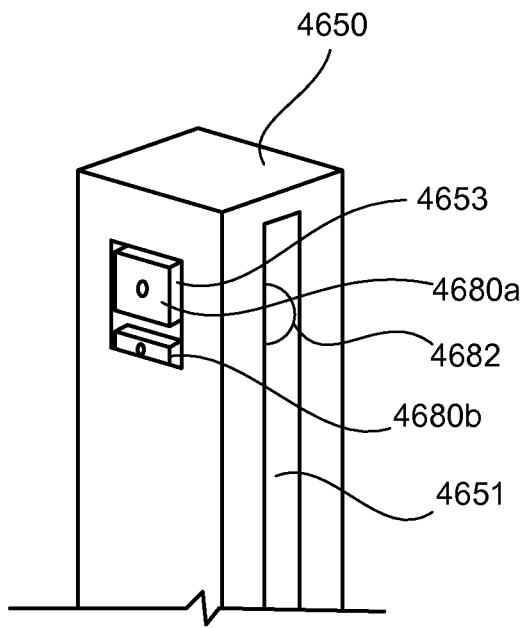
FIG. 47 is a perspective view of a cartridge according to an embodiment of the invention.

FIG. 47 is a perspective view of the anchor 4680*a*, the coupling member 4682, and the anchor 4680*b* disposed within a cartridge 4650. The cartridge 4650 may be coupled to and used with a delivery tool as described above. The cartridge 4650 is configured to retain or house the anchors 4680*a* and 4680*b*. The cartridge 4650 defines a slot 4651. The coupling member 4682 extends from the slot 4651. In other embodiments, the cartridge 4650 does not define a slot and the lumen or cavity of the cartridge 4650 is configured to house or retain the coupling member. In use, the cartridge 4650 may be coupled to a delivery tool and a carrier of the delivery tool may engage the anchor 4680*a* (for example by extending through the lumen 4685*a* defined by the anchor 4680*a*) and move the anchor 4680*a* out of or away from the cartridge 4650 (such as through opening 4653 of the cartridge 4650). In some embodiments, the cartridge 4650 includes a biasing member such as a spring that is configured to move anchor 4680*b* in place within the cartridge 4680 for engagement with the carrier. Accordingly, the anchors 4680*a* and 4680*b* may be used to couple portions of bodily tissue together or to help couple an implant to bodily tissue.

Figure 48:
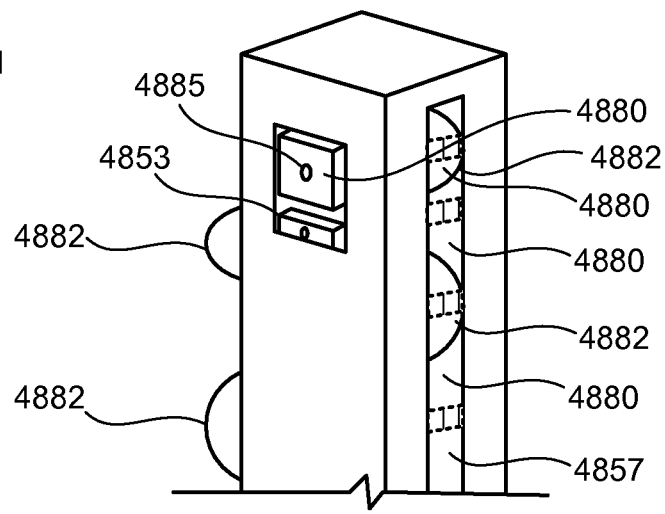
FIG. 48 is a perspective view of a cartridge according to an embodiment of the invention.

While the anchor mechanism 4677 includes two anchors, other anchor mechanisms may include more than two anchors that are coupled together. For example, in some embodiments, three, four, or more anchor mechanisms are coupled together via coupling members. FIG. 48 is a perspective view of a cartridge 4850 that has a coupling mechanism that includes more than two anchors 4880 coupled together via coupling members 4882.

Figure 49:
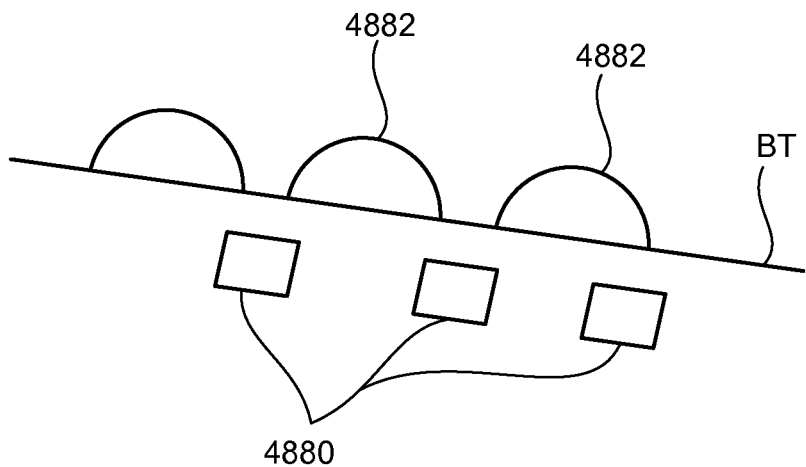
FIG. 49 is a schematic illustration of an anchor mechanism disposed within bodily tissue.

The cartridge 4850 may be coupled to and used with a delivery tool as described above. The cartridge 4850 is configured to retain or house the anchors 4880. The cartridge 4850 defines slots 4851 (only one illustrated) disposed on opposite sides of the cartridge 4850. The coupling members 4882 extend from the slots 4851. In other embodiments, the cartridge 4850 does not define a slot and the lumen or cavity of the cartridge 4850 is configured to house or retain the coupling members. In use, the cartridge 4850 may be coupled to a delivery tool and a carrier of the delivery tool may engage the anchors 4880 (for example by extending through a lumen 4885 defined by the anchor 4880) and move the anchor 4880 out of or away from the cartridge 4850 (such as through opening 4853 of the cartridge 4850). In some embodiments, the cartridge 4850 includes a biasing member such as a spring that is configured to move each successive anchor 4880 in place within the cartridge 4880 for engagement with the carrier. Accordingly, as schematically illustrated in FIG. 49, the anchors 4880 may be serially inserted into bodily tissue BT to couple portions of bodily tissue together or to help couple an implant to the bodily tissue.

Figure 50:
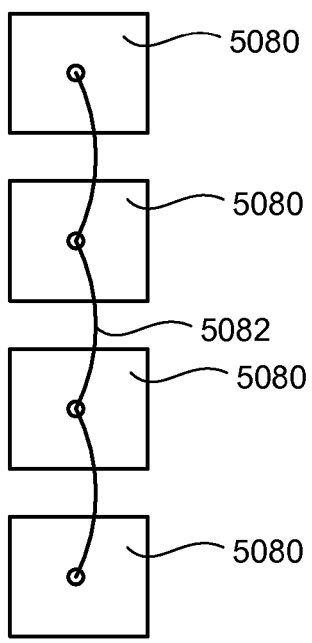
FIG. 50 is a perspective view of anchor according to an embodiment of the invention.

In some embodiments, the anchors 4880 are coupled together via a plurality of separate coupling members 4882. For example, end portions of the coupling members 4882 can be fixedly coupled to the anchors 4880. In other embodiments, a single coupling member is used to couple the plurality of anchors 4880 together. For example, as illustrated in FIG. 50, a plurality of anchors 5080 may be threaded along the single coupling member 5082. In some embodiments, the anchors 5080 are fixedly coupled to the single coupling member 5082. In other embodiments, the anchors 5080 are threaded along the single coupling member 5082 such that some of the anchors 5080 may slide along the coupling member 5082. For example, in the illustrated embodiment, the coupling member 5082 is fixedly coupled to the end anchors but the middle anchors are slidably coupled to the coupling member 5082.

Figure 51:
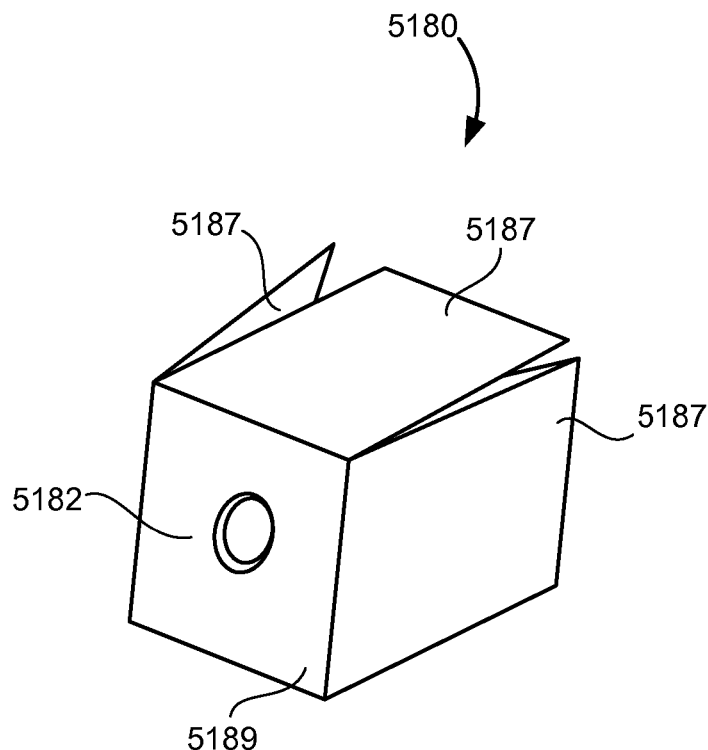
FIGS. 51-53 are perspective views of anchors according to embodiments of the invention.

FIG. 51 is a perspective view of an anchor 5180 according to an embodiment of the invention. The anchor 5180 includes or defines a lumen 5182 that is configured to receive a carrier or a portion of a carrier member of a delivery tool. The anchor 5180 includes projections 5187 that extend from a body portion 5189 of the anchor 5180. In the illustrated embodiment, the projections 5187 extend from the body portion 5189 at an angle. The projections or barbs 5187 are configured to help secure the anchor 5180 in place within bodily tissue and help prevent the anchor 5180 from being pulled out of the bodily tissue.

Figure 52:
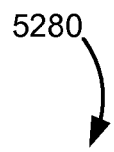

FIG. 52 is a perspective view of an anchor 5280 according to an embodiment of the invention. The anchor 5280 includes or defines a lumen 5282 that is configured to receive a carrier or a portion of a carrier member of a delivery tool. Specifically, the anchor 5280 includes a sidewall 5281 that defines a portion of the lumen 5282. The sidewall 5281 includes a curved or funnel-like shape. The curved or funnel-like shape of the sidewall 5281 is configured to help facilitate the entry of the carrier into the lumen 5282. In some embodiments, if the carrier contacts the sidewall 5281 rather than immediately extending into the lumen 5282, the carrier will be guided or forced along the funnel-like sidewall 5281 towards the lumen 5282 or a center portion of the lumen 5282.

Figure 53:
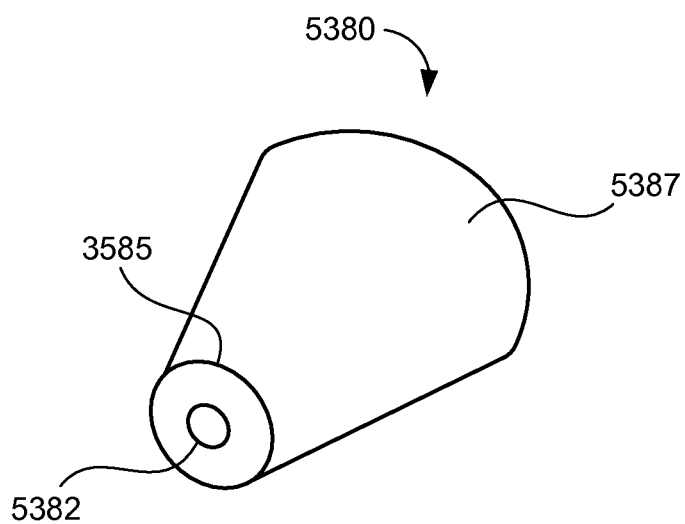

FIG. 53 is a perspective view of an anchor 5380 according to an embodiment of the invention. The anchor 5380 includes or defines a lumen 5382 that is configured to receive a carrier or a portion of a carrier member of a delivery tool. The anchor 5380 includes a tapered shape. Specifically, the leading or distal end 5385 is smaller than the trailing or proximal end 5387. Accordingly, the as anchor 5380 is placed or advanced through bodily tissue, the leading end portion 5385 helps create the passageway through the bodily tissue. Once placed in the body tissue, the trailing end portion 5387 helps retain the anchor 5380 in place within the bodily tissue and helps prevent the anchor 5380 from being pulled out of the tissue.

Figure 54:
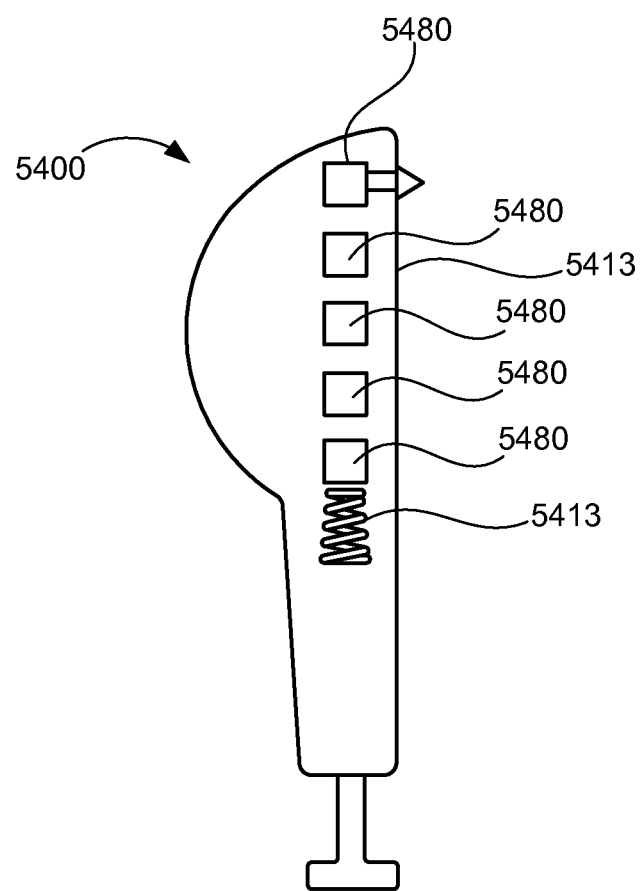
FIG. 54 is a perspective view of medical device according to an embodiment of the invention.

FIG. 54 is a perspective view of a medical device 5400 according to an embodiment of the invention. The medical device 5400 includes a delivery tool 5410 that is configured to deliver anchors or anchor members to locations within a body of a patient. In the illustrated embodiment, the anchors or anchor members 5480 are disposed our retained in a cartridge 5450. The cartridge 5450 is fixedly coupled to the delivery tool 5410. For example, in some embodiments, the cartridge 5450 is unitarily or monolithically formed with the delivery tool 5410. In the illustrated embodiment, a spring or other biasing member 5453 is disposed within the cartridge 5450 and is configured to serially place the anchors 5480 in position for contact and engagement by a carrier of the delivery tool 5410. In the illustrated embodiment, the cartridge 5450 is vertically or parallel to an longitudinal axis of the delivery tool 5410.

Also, in the illustrated embodiment, the face or front surface 5413 of the delivery tool 5410 is planar. The planar face or front surface 5413 is configured to contact bodily tissue to help prevent over insertion of the anchors 5480 into the bodily tissue.

Figure 55:
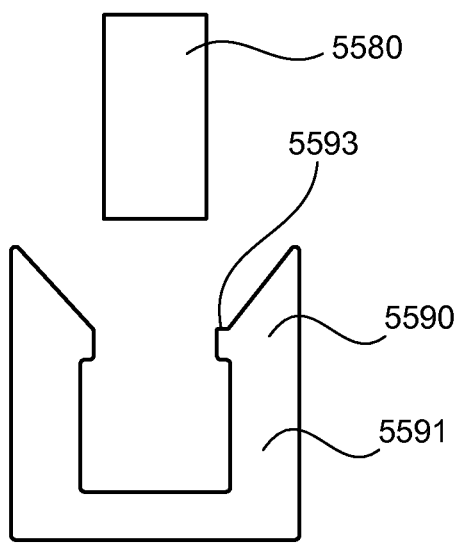
FIGS. 55 and 56 are side views of an anchor and a catch according to an embodiment of the invention.
Figure 56:
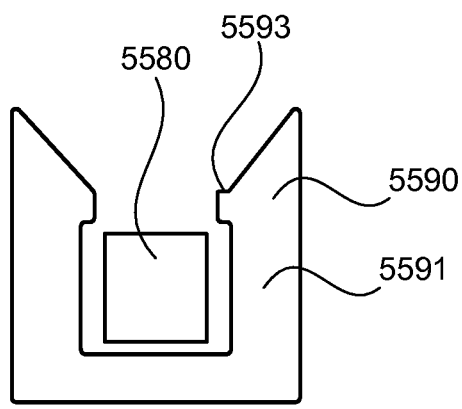

FIGS. 55 and 56 are side views of an anchor 5580 and a catch 5590. The anchor 5580 is configured to be received by the catch 5590. In the illustrated embodiment, the catch 5590 includes portions 5591 that are configured to flex to receive the anchor 5580. The catch 5590 also includes retention portions 5593 that are configured to help retain the anchor 5580 in place within the catch 5590. In some embodiments, the anchor and catch can be coupled to a coupling member. In some embodiments, the coupling member is formed of an elastic material or is otherwise configured to stretch.

Figure 57:
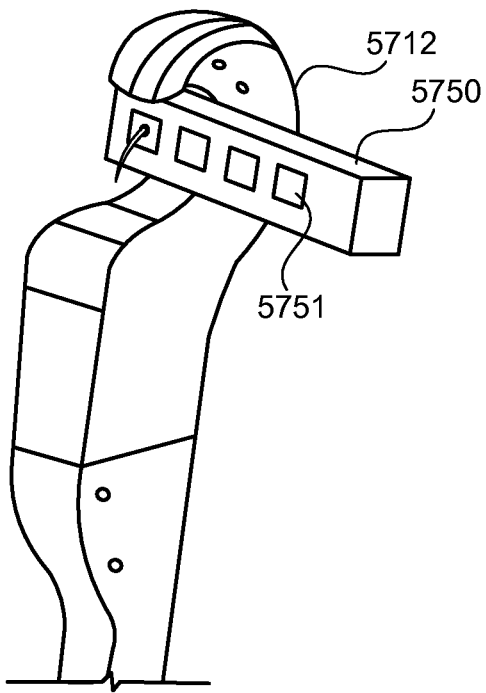
FIG. 57 is a perspective view of a medical device according to an embodiment of the invention.

FIG. 57 is a perspective view of a delivery tool 5710 according to an embodiment of the invention. The delivery tool 5710 is coupled to a cartridge 5750 that is disposed horizontally. In the illustrated embodiment, the cartridge 5750 is disposed orthogonal to the longitudinal axis of the delivery tool 5710. In the illustrated embodiment, the cartridge 5750 includes a spring 5751 or other biasing member that is configured to advance the anchors horizontally within the cartridge 5750.

FIG. 58 is a perspective view of a cartridge 5850 according to an embodiment of the invention. The cartridge 5850 includes a movable floor 5853. The movable floor or member 5853 is configured to be moved when the carrier 5812 is advanced towards and into the cartridge 5850. Specifically, the floor 5853 is configured to move into a position to help prevent the second anchor in the cartridge 5850 from interfering with the movement of the first anchor in the cartridge 5850 by the carrier 5812.

FIG. 59 is a perspective view of a carrier member 5912 according to an embodiment of the invention. The carrier member 5912 includes a projection member 5917. The projection member 5917 extends from the carrier member 5912 and is disposed below the distal portion of the carrier member 5912. The projection member 5917 is configured to extend between the top two anchors within a cartridge. Accordingly, the projection member 5917 helps prevent the second anchor from getting in the way of or prohibiting the movement of the top anchor when the carrier moves or places a force on the top anchor (as best illustrated in FIG. 60).

In other embodiments, the projection member or separator is separate from the carrier member. In such embodiments, the separator may be moved via the actuator that is operatively coupled to the carrier or may be operatively coupled to a separate actuator.

Figure 61:
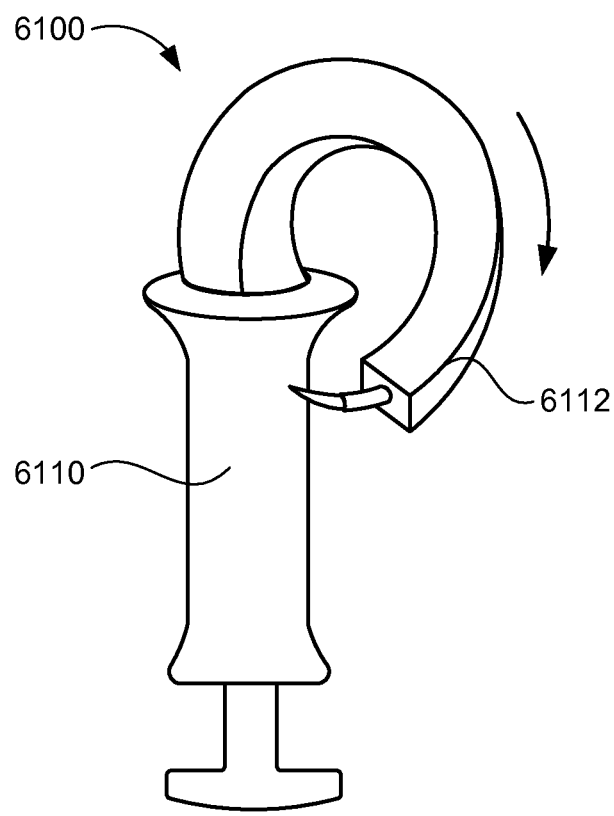
FIG. 61 is a perspective view of a medical device according to an embodiment of the invention.

FIG. 61 is a perspective view of a medical device 6100 according to an embodiment of the invention. The medical device 6100 includes a carrier 6112. The carrier 6112 is disposed horizontally. Accordingly, anchors may be placed in a perpendicular position with respect to the delivery tool 6110.

Figure 62:
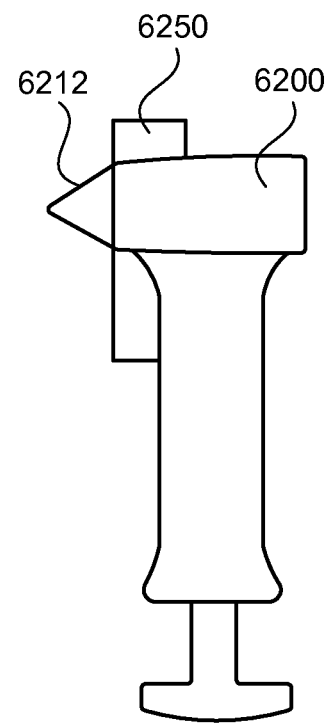
FIG. 62 is a side view of a medical device according to an embodiment of the invention.
Figure 63:
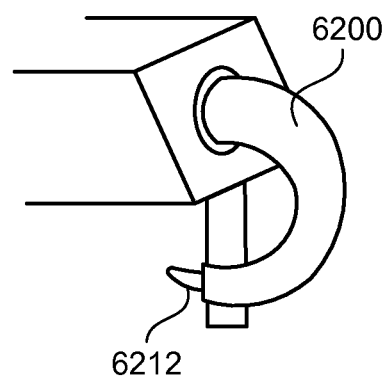
FIG. 63 is a top view of the medical device of FIG. 62.
Figure 64:
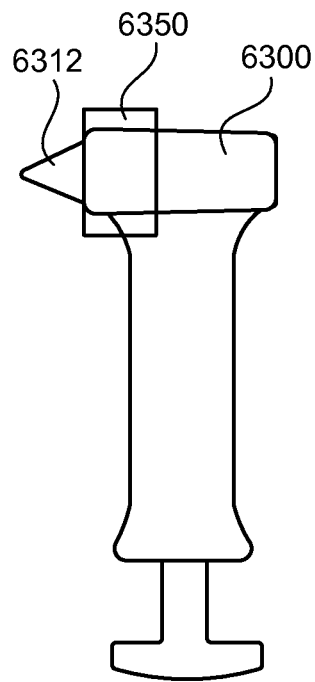
FIG. 64 is a side view of a medical device according to an embodiment of the invention.
Figure 65:
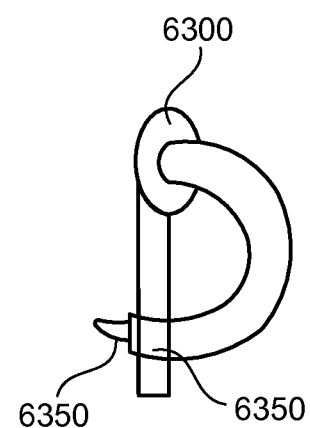
FIG. 65 is a top view of the medical device of FIG. 64.

FIG. 62 is a side view of a medical device 6200 according to an embodiment of the invention. FIG. 63 is a top view of the medical device 6200. The medical device 6200 includes a carrier 6212 that is curved and extends horizontally. In one embodiment, the carrier 6212 extends in a direction orthogonal to the longitudinal axis of the medical device 6200. In the illustrated embodiment, the medical device 6200 includes a cartridge 6250 that is disposed vertically (or parallel to the longitudinal axis of the medical device 6200). In other embodiments, as illustrated in FIGS. 64 and 65, the medical device 6300 includes a cartridge 6350 that is disposed or extends horizontally (or orthogonal to the longitudinal axis of the medical device). In some embodiments, a catch is not required. In other words the carrier may function to insert the anchor directly into bodily tissue (or through an implant and into bodily tissue).

Figure 66:
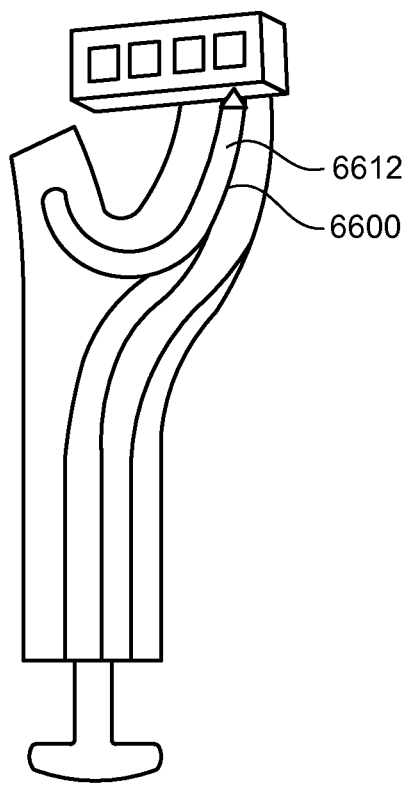
FIG. 66 is a side view of a medical device according to an embodiment of the invention.

FIG. 66 is a side view of a medical device 6600 according to an embodiment of the invention. In the illustrated embodiment, the medical device 6600 includes a carrier 6612 that extends forward or distally. Additionally, in the illustrated embodiment, the carrier 6612 is curved.

Figure 67:
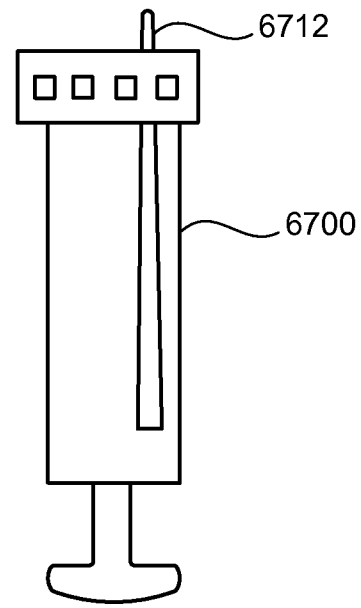
FIG. 67 is a side view of an embodiment of the invention.

FIG. 67 is a side view of a medical device 6700 according to an embodiment of the invention. In the illustrated embodiment, the medical device 6700 includes a carrier 6712 that extends forward or distally. Additionally, in the illustrated embodiment, the carrier 6712 is linear or substantially linear. In some embodiments, the carrier 6712 moves the anchor directly into bodily tissue (rather than moving the anchor towards a catch).

Figure 68:
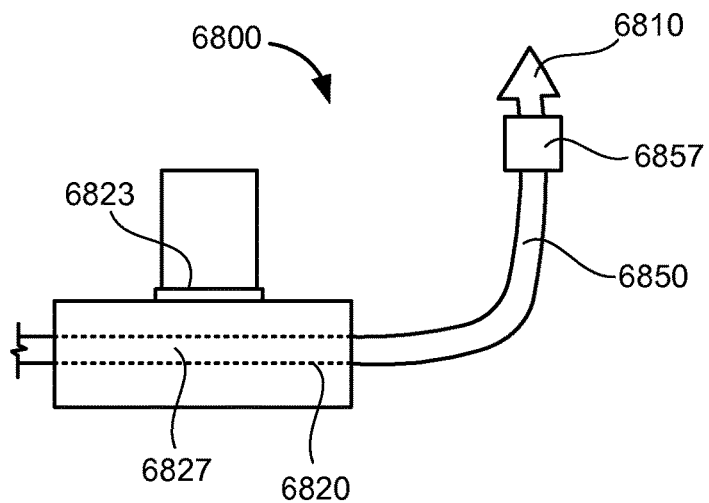
FIGS. 68 and 69 are side views of devices according to an embodiment of the invention.
Figure 69:
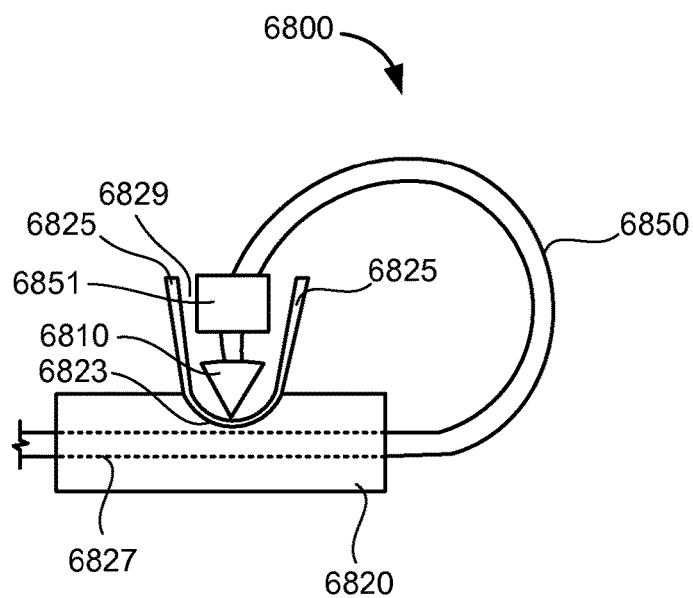

FIGS. 68 and 69 are side perspective views of a medical device 6800 according to an embodiment of the invention. The medical device 6800 includes a needle 6810, a catch 6820, and a coupling member 6850. The catch 6820 is shown in see-though in FIGS. 68 and 69.

In the illustrated embodiment, the medical device 6800 may be placed within a body of a patient to help couple or fix an implant within the body of the patient. For example, the needle 6810, the catch 6820, and the coupling member 6850 may collectively form a loop around or through an implant and bodily tissue to couple the implant to the bodily tissue.

In the illustrated embodiment, the coupling member 6850 is a suture and is coupled to the needle 6810. The catch 6820 is in the shape of a T and defines a first lumen 6827 and a second lumen 6829. The coupling member 6850 is configured to be passed through the first lumen 6827 and be frictionally coupled to the sidewall that forms the first lumen 6827. Accordingly, the coupling member 6850 can be passed through the first lumen 6827 and coupled therein.

The needle 6810 is configured to be coupled within the second lumen 6829. For example, in the illustrated embodiment, the catch 6820 includes a flexible or bendable element or member 6823. The needle 6810 is configured to be inserted into the lumen 6829 and contact the flexible or bendable member 6823. The needle 6810 or the force of the needle 6810 contacting the flexible or bendable member 6823 may cause the member 6823 to bend. In the illustrated embodiment, the bending of the member 6823 is configured to close or partially close the first lumen 6827 to help engage and retain the coupling member 6850 within the first lumen 6827. In the illustrated embodiment, the flexible member 6823 includes wings or projections 6825 that are configured to wrap around or grasp a portion 6851 of the coupling member 6850 to help retain the needle 6810 within the second lumen 6829.

Accordingly, in use, the medical device 6800 can be placed within the body of a patient. The coupling member 6850 can be passed through the first lumen 6827. The coupling member 6850 can then be passed through bodily tissue and through an implant. The needle 6810 may be configured to facilitate the passing of the coupling member through the implant and the bodily tissue. The needle 6810 can then be inserted into the second lumen 6829. Once the needle 6810 is inserted into the second lumen 6829, the needle 6810 is coupled or fixed within the lumen 6829. In such an embodiment, the implant is thereby fixed or coupled to the bodily tissue via the medical device 6800.

Figure 70:
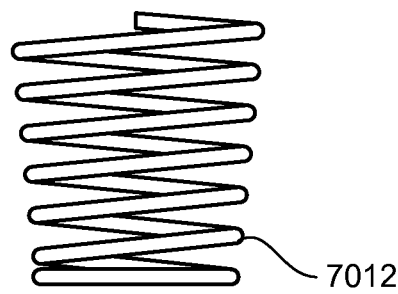
FIG. 70 is a perspective view of a carrier according to an embodiment of the invention.
Figure 71:
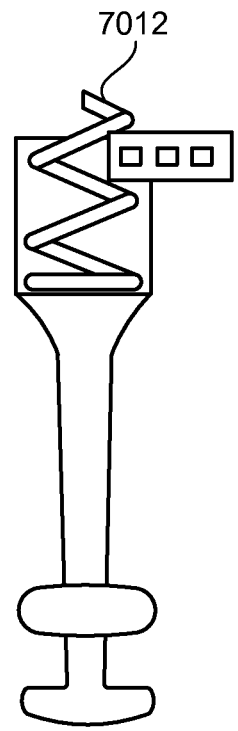
FIGS. 71 and 72 are side views of a medical device according to an embodiment of the invention.
Figure 72:
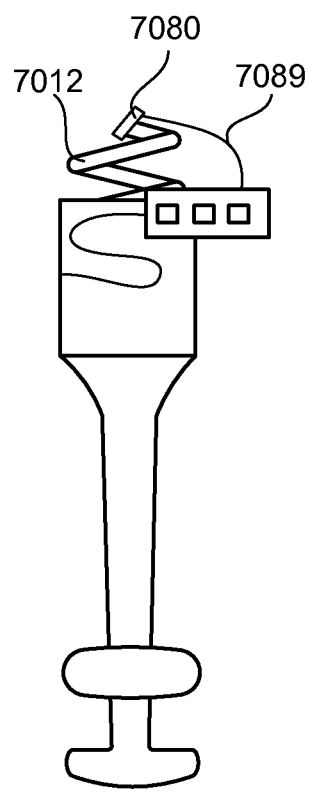
Figure 73:
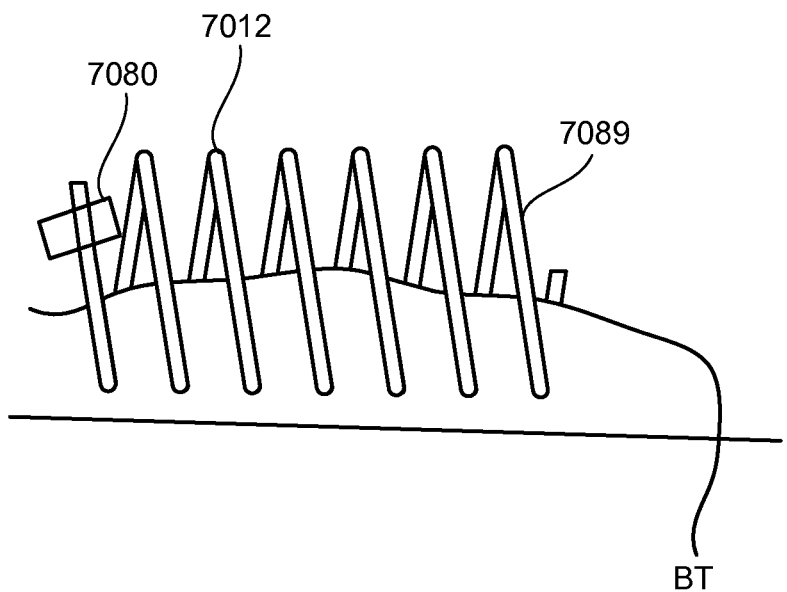
FIG. 73 is a schematic view of the carrier of FIG. 70 and an anchor disposed within a body of a patient.
Figure 74:
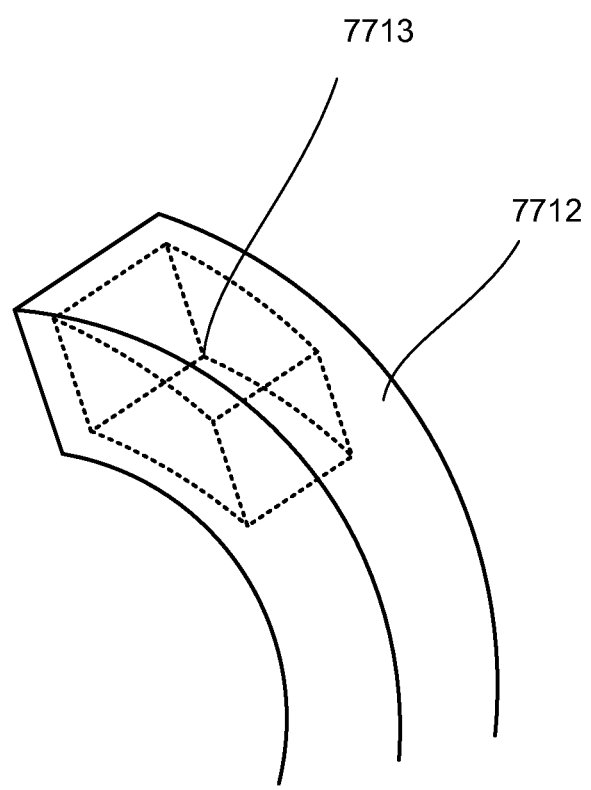
FIGS. 74 to 87 illustrate carrier and anchor engagement systems.
Figure 75:
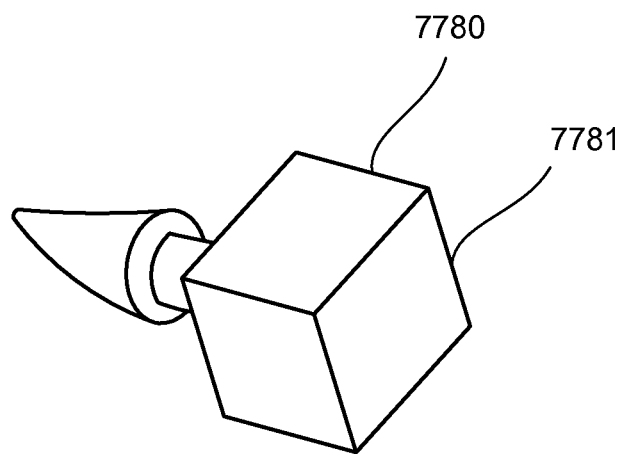

FIG. 70 is a perspective view of a carrier 7012 according to an embodiment of the invention. The carrier 7012 has a helical shape. In other words, the carrier 7012 forms several loops or curls. As best illustrated in FIGS. 71 and 72, as the carrier 7012 is advanced from its first position to its second position, it twists or rotates. In some embodiments, the actuator may be twisted to cause the carrier 7012 to advance and twist. Accordingly, as the carrier 7012 is advanced through a cartridge it is coupled to or engages an anchor 7080. In the illustrated embodiment, the anchor 7080 is coupled to a suture 7089. As illustrated in FIG. 73, as the carrier 7012 moves the anchor 7080 and suture 7089 though bodily tissue BT, the suture will be passed though the bodily tissue several times to create a continuous stitch. In some embodiments, the suture can be used to pass through an implant to couple an implant to the bodily tissue.

Figure 76:
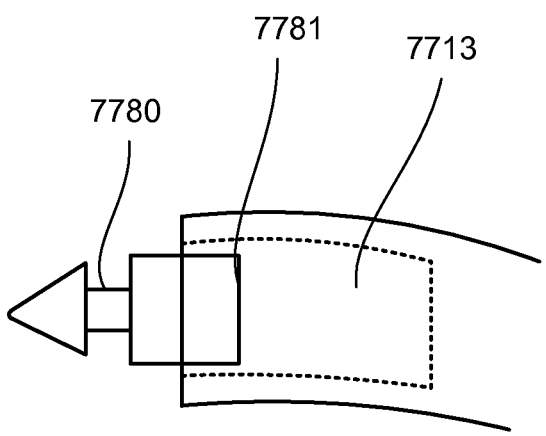
Figure 77:
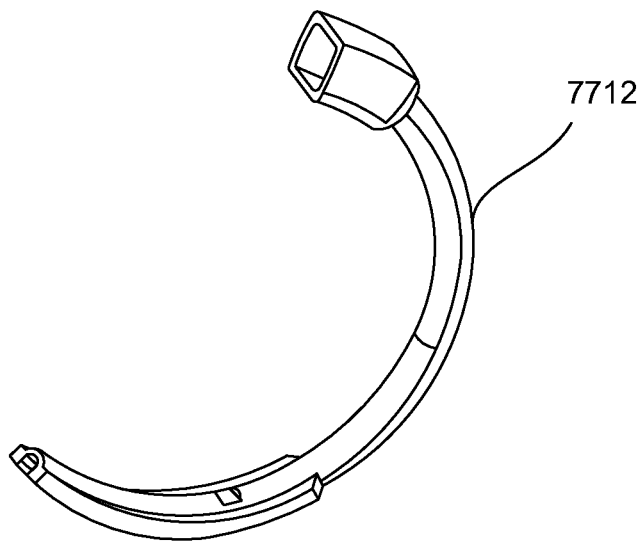
Figure 78:
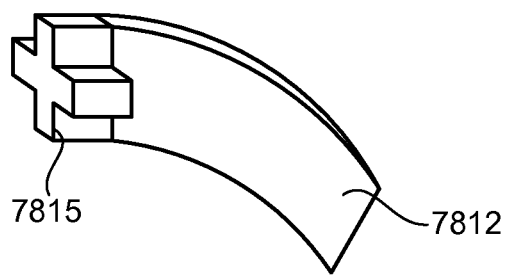

FIGS. 74 to 77 illustrate a carrier 7712 and an anchor 7780 and a coupling or engaging between the carrier 7712 and the anchor 7780. In the illustrated embodiment, the carrier 7712 defines a cavity 7713. The cavity 7713 is rectangular or square in cross-section. The anchor 7780 includes an end portion 7781 that is rectangular or square. As best illustrated in FIG. 76, the end portion 7781 of the anchor 7780 is configured to be received by the cavity 7713 of the carrier 7712.

Figure 79:
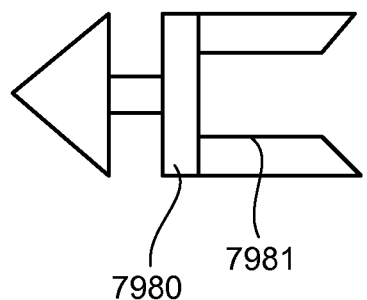
Figure 80:
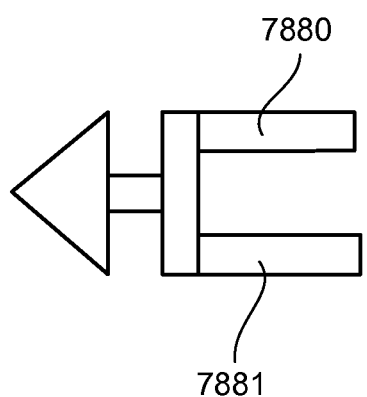
Figure 81:
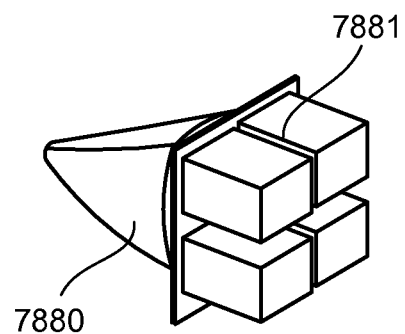

FIGS. 78 to 81 illustrate a carrier 7812 and an anchor 7880 and a coupling or engaging between the carrier 7812 and the anchor 7880. In the illustrated embodiment, the carrier 7812 defines or includes a projection 7815 that is in the shape of a plus sign. The anchor 7880 includes posts 7881 that collectively define an opening or cavity in the shape of a plus sign. In the illustrated embodiment, the anchor 7880 includes a sharp end portion that is configured to penetrate or pierce bodily tissue. In the illustrated embodiment, the projection 7815 is configured to be received by the opening or cavity of the anchor 7880. In some embodiments, as illustrated in FIG. 79, the posts 7981 of the anchor 7980 may include an angled or curved surface.

Figure 82:
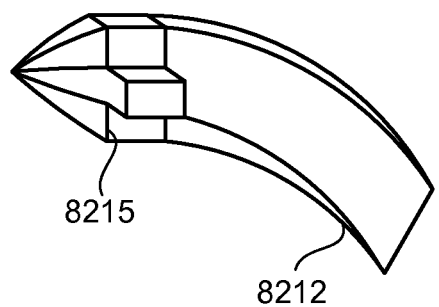
Figure 83:
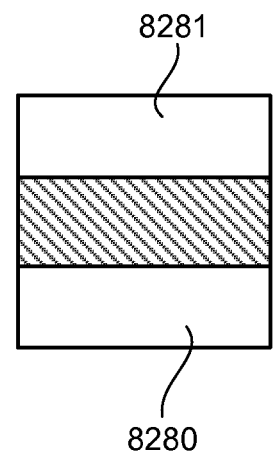
Figure 84:
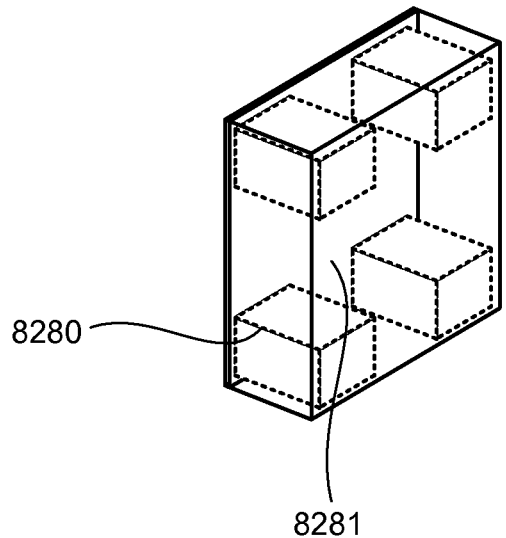

FIGS. 82 to 84 illustrate a carrier 8212 and an anchor 8280 and a coupling or engaging between the carrier 8212 and the anchor 8280. In the illustrated embodiment, the carrier 8212 defines or includes a projection 8215 that is in the shape of a plus sign. The anchor 8280 includes an opening or cavity 8281 in the shape of a plus sign. In the illustrated embodiment, the projection 8215 includes a sharp end portion that is configured to penetrate or pierce bodily tissue. In the illustrated embodiment, the projection 7815 is configured to be received by the opening or cavity 8281 of the anchor 7880.

Figure 85:
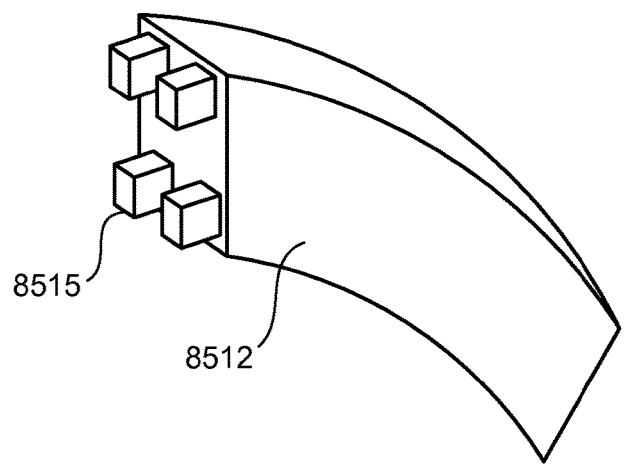
Figure 86:
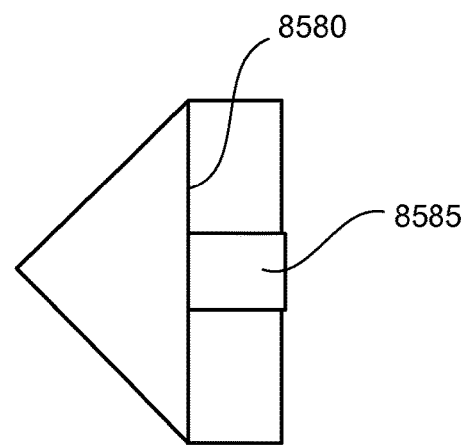
Figure 87:
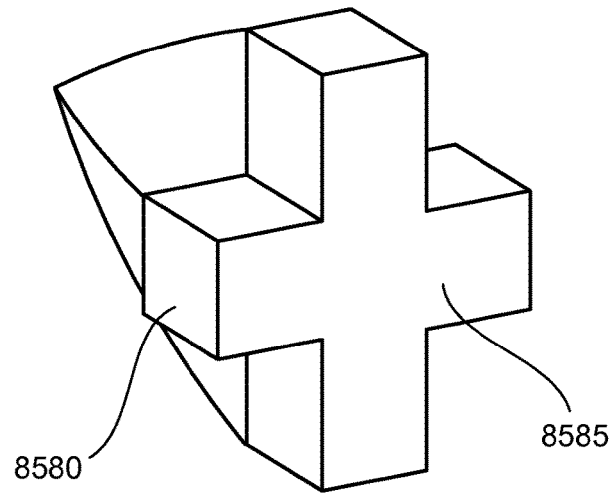

FIGS. 85-87 illustrate a carrier 8512 and an anchor 8580 and a coupling or engaging between the carrier 8512 and the anchor 8580. In the illustrated embodiment, the anchor 8580 defines or includes a projection 8585 that is in the shape of a plus sign. The carrier 8512 includes an opening or cavity 8515 in the shape of a plus sign. In the illustrated embodiment, the projection 8585 is configured to be received by the opening or cavity 8515.

Figure 88:
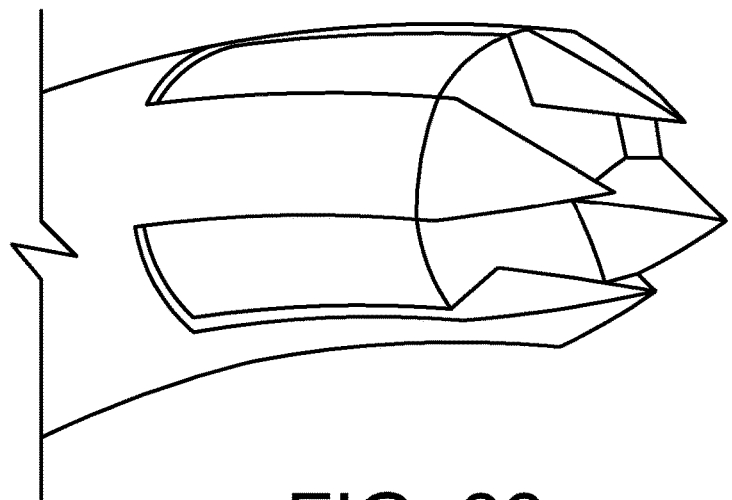
FIG. 88 is a perspective view of an end portion of a carrier according to an embodiment of the invention.

FIG. 88 is a perspective view of an end portion of a carrier 8812 according to an embodiment of the invention. The carrier 8812 includes a set of projections that have tapered or sharp end portions.

Figure 89:
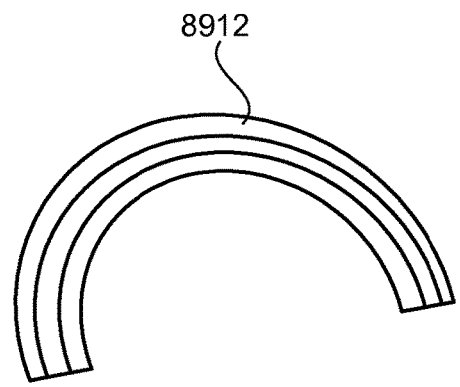
FIG. 89 is a side view of a carrier in accordance with an embodiment of the invention.
Figure 90:
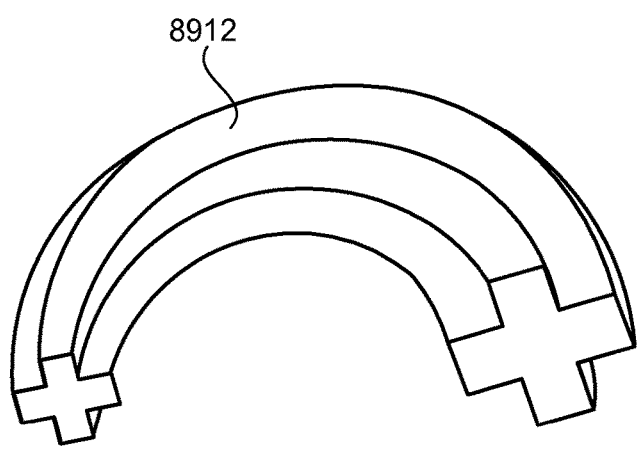
FIG. 90 is a perspective view of the carrier of FIG. 89.
Figure 91:
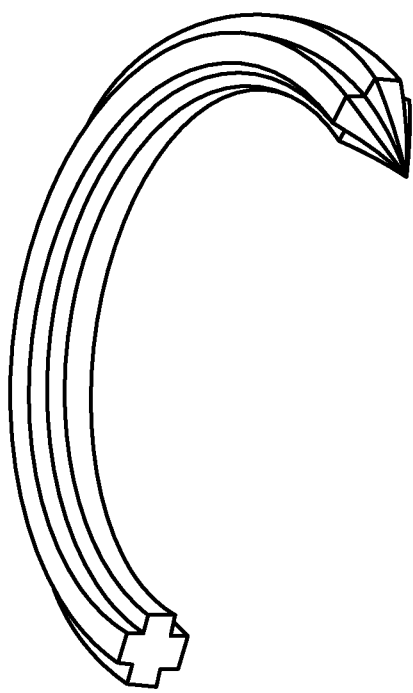
FIGS. 91 to 95 illustrate carriers according to other embodiments of the invention.
Figure 92:
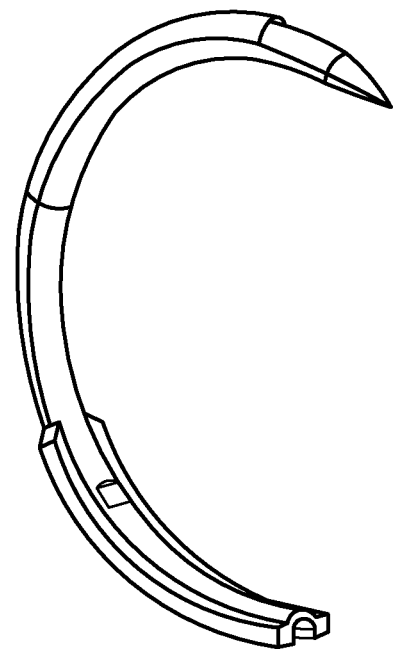
Figure 93:
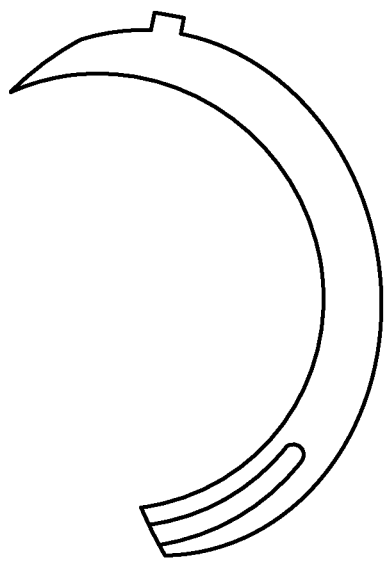
Figure 94:
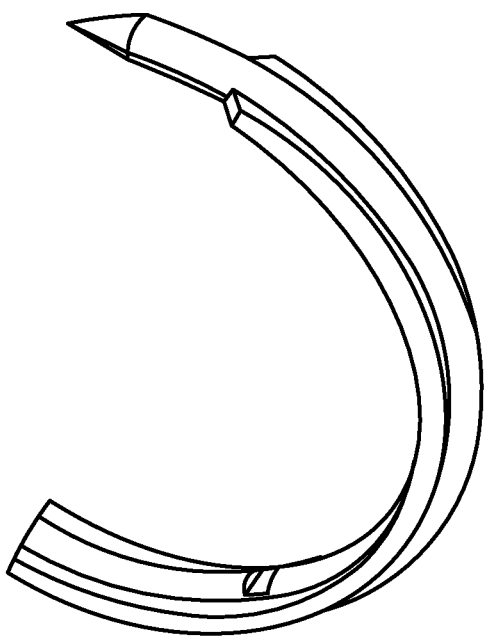
Figure 95:
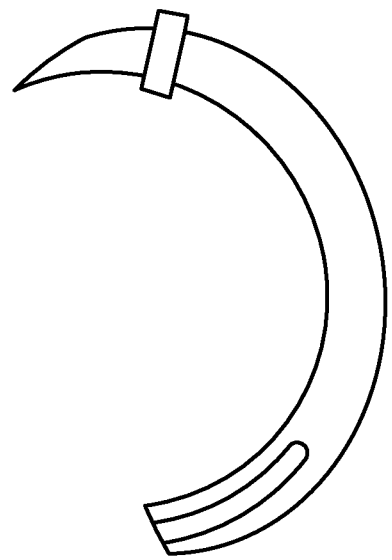

FIG. 89 is a side view of a carrier 8912 in accordance with an embodiment of the invention. FIG. 90 is a perspective view of the carrier 8912. The carrier 8912 has a cross-section that is in the shape of a plus sign. In other embodiments, the carrier has a cross-section that has a different shape, such as a circle, an oval or a rectangle.

FIGS. 91 to 95 illustrate carriers according to other embodiments of the invention. The carriers include different shaped shoulder members and body portions that have different cross-sectional shapes.

Figure 96:
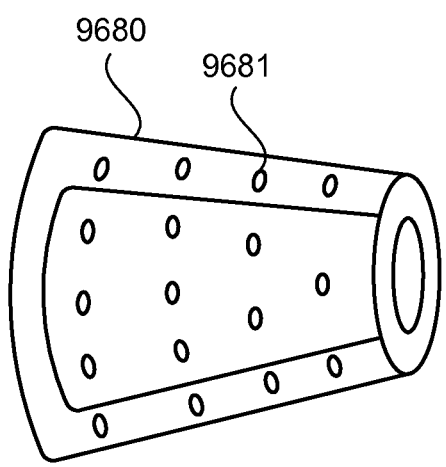
FIG. 96 is an anchor member according to an embodiment of the invention.
Figure 97:
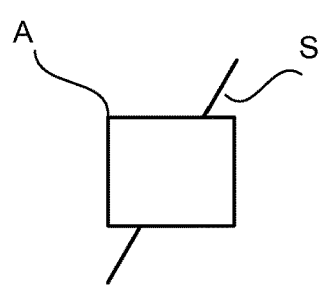
FIGS. 97 to 104 illustrate anchors according to embodiments of the invention.
Figure 98:
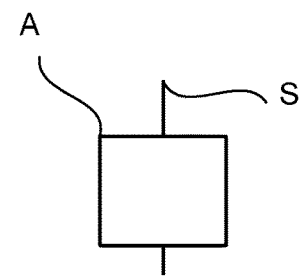
Figure 99:
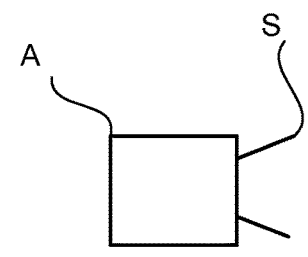
Figure 100:
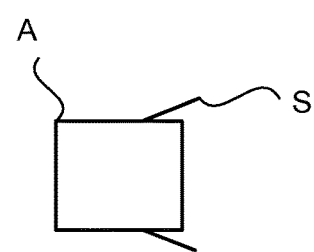
Figure 101:
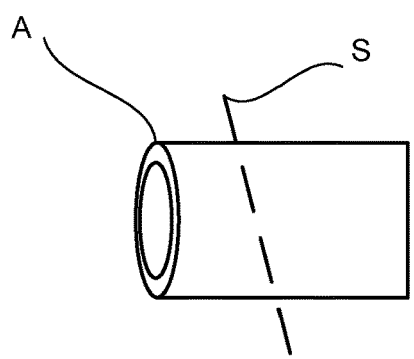
Figure 102:
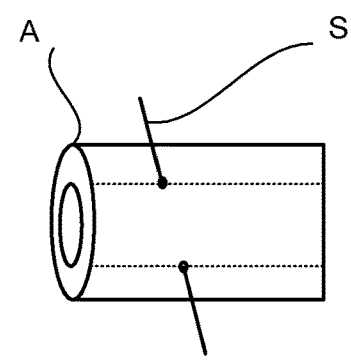
Figure 103:
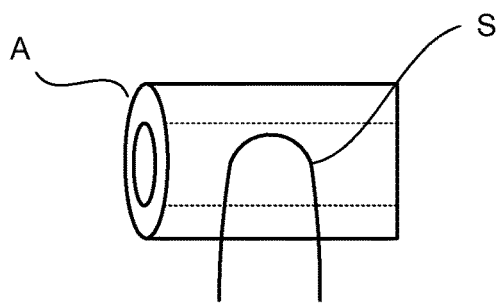
Figure 104:
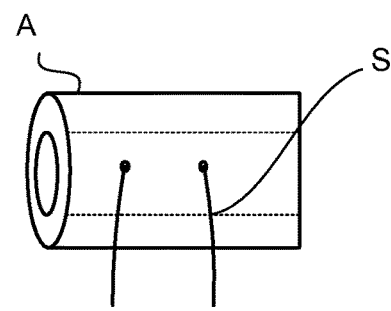

FIG. 96 is an anchor member 9680 that defines openings 9681. The openings 9681 are configured to promote or allow ingrowth of bodily tissue.

FIGS. 97 to 104 illustrate anchors A with sutures or coupling members S attached at various locations along the anchor. The coupling member may be coupled to or through any portion of the anchors. For example, the sutures or coupling members may be coupled to a side portion of the anchor or to an end portion of the anchor.

In some embodiments, a medical device includes a delivery tool having a carrier member and a cartridge coupled to the delivery tool. The cartridge defines an opening. The cartridge being configured to retain an anchor defining a lumen. The carrier member having a retracted configuration and an extended configuration. The carrier member being configured to extend through the lumen defined by the anchor and through the opening defined by the cartridge when the cartridge is coupled to the delivery tool and the carrier member is in its extended configuration. In some embodiments, the cartridge defines a cavity, the cavity being configured to retain the anchor. In some embodiments, the cartridge is configured to retain a plurality of anchors. In some embodiments, the delivery tool includes an actuation member configured to move the carrier member from its retracted configuration to its extended configuration. In some embodiments, the carrier member is retracted form the cartridge when the carrier member is in its refracted configuration. In some embodiments, the cartridge is fixedly coupled to the delivery tool. In some embodiments, the cartridge is removably coupled to the delivery tool. In some embodiments, the cartridge is integrally formed with at least a portion of the delivery tool. In some embodiments, the delivery tool includes a projection, the cartridge defines an aperture, the projection being configured to at least partially extend into the aperture to help removably couple the cartridge to the delivery tool.

In some embodiments, a method of securing an implant includes positioning a device proximate to the implant, the device having a delivery tool, an anchor, and a catch, the anchor being removably coupled to the delivery tool, the catch being removably coupled to the delivery tool; passing the anchor through the implant; coupling the anchor to the catch; removing the anchor from the delivery tool; and removing the catch from the delivery tool. In some embodiments, the delivery tool includes a carrier member. In some embodiments, the anchor defines a lumen, the carrier being configured to extend through the lumen defined by the anchor. In some embodiments, the delivery tool includes a cartridge, the cartridge being configured to retain the anchor. In some embodiments, the delivery tool includes a cartridge, the cartridge being configured to retain the anchor and the catch. In some embodiments, the delivery tool includes a cartridge, the cartridge being configured to retain the anchor, the cartridge being configured to be removably coupled to the delivery tool.

In some embodiments, a medical device includes a delivery tool having a carrier member; and a cartridge coupled to the delivery tool. The cartridge defining an opening. The cartridge being configured to retain an anchor defining a lumen. The carrier member having a retracted configuration and an extended configuration. The carrier member being configured to extend through the lumen defined by the anchor and through the opening defined by the cartridge when the cartridge is coupled to the delivery tool and the carrier member is in its extended configuration. In some embodiments, the cartridge defines a cavity, the cavity being configured to retain the anchor. In some embodiments, the cartridge is configured to retain a plurality of anchors. In some embodiments, the delivery tool includes an actuation member configured to move the carrier member from its retracted configuration to its extended configuration. In some embodiments, the carrier member is retracted form the cartridge when the carrier member is in its refracted configuration. In some embodiments, the cartridge is fixedly coupled to the delivery tool. In some embodiments, the cartridge is removably coupled to the delivery tool. In some embodiments, the cartridge is integrally formed with at least a portion of the delivery tool. In some embodiments, the delivery tool includes a projection, the cartridge defines an aperture, the projection being configured to at least partially extend into the aperture to help removably couple the cartridge to the delivery tool.

In some embodiments, a medical device includes a delivery tool having a carrier member; an anchor removably coupled to the delivery tool; and a catch being removably coupled to the delivery tool. The carrier member having a refracted configuration and an extended configuration, the carrier member being configured to move the anchor towards the catch when the carrier moves from its retracted configuration to its extended configuration. In some embodiments, the anchor defines a lumen, the carrier being configured to extend through the lumen defined by the anchor. In some embodiments, the delivery tool includes a cartridge, the cartridge being configured to retain the anchor. In some embodiments, the delivery tool includes a cartridge, the cartridge being configured to retain the anchor and the catch. In some embodiments, the delivery tool includes a first cartridge and a second cartridge, the first cartridge being configured to retain the anchor, the second cartridge being configured to retain the catch. In some embodiments, the delivery tool includes a cartridge, the cartridge being configured to retain the anchor, the cartridge being configured to be removably coupled to the delivery tool. In some embodiments, the delivery tool includes a cartridge, the cartridge being configured to retain the anchor, the cartridge being integrally formed with at least a portion of the delivery tool. In some embodiments, the anchor is configured to be coupled to the catch. In some embodiments, the device includes a filament having a first end portion coupled to the anchor and a second end portion coupled to the catch.

In some embodiments, a method of securing an implant within a body of a patient, includes inserting a device into a body of the patient, the device having a delivery tool, an anchor and a catch, the delivery tool including a carrier member, the anchor being removably coupled to the delivery tool, the catch being removably coupled to the delivery tool; passing the anchor through the implant and through bodily tissue; coupling the anchor to the catch; removing the anchor from the delivery tool; and removing the catch from the delivery tool. In some embodiments, the method includes removing the delivery tool from the body of the patient.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device, comprising:
a delivery tool having a distal end portion, and a carrier member, the distal end portion defining a carrier opening and a catch location, the catch location being disposed proximally from the carrier opening, the carrier member configured to move along a travel path from a position within the distal end portion, out of the carrier opening, and into a portion of a catch, the catch being removably coupled to the distal end portion, at least a portion of the carrier member being curved, at least a portion of the travel path being curved, the distal end portion defining a slot; and
a cartridge coupled to the distal end portion of the delivery tool, the cartridge having a longitudinal axis extending from a first end portion to a second end portion, the cartridge configured to be inserted into the slot, the cartridge including a coupling member configured to couple the cartridge to the delivery tool in response to the cartridge being disposed within the slot of the distal end portion, the cartridge defining an opening, the opening of the cartridge being disposed within the travel path of the carrier member, the cartridge being configured to retain an anchor defining a lumen, the cartridge including a biasing member, the biasing member being disposed within a cavity of the cartridge, the biasing member being disposed proximally of the opening of the cartridge, the anchor being attached to the catch via an attachment member,
wherein the distal end portion of the delivery tool includes a projection, the coupling member of the cartridge includes an aperture, the projection being configured to at least partially extend into the aperture to couple the cartridge to the delivery tool,
wherein the cartridge is coupled to the delivery tool such that a portion of the travel path of the carrier member is disposed between the biasing member of the cartridge and the projection of the delivery tool, and
wherein the carrier member is configured to extend through the lumen defined by the anchor and through the opening defined by the cartridge in response to the carrier member moving along the travel path.

2. The medical device of claim 1, wherein the cavity is configured to retain the anchor.

3. The medical device of claim 1, wherein the cartridge is configured to retain a plurality of anchors.

4. The medical device of claim 1, wherein the delivery tool includes an actuation member configured to move the carrier member along the travel path.

5. The medical device of claim 1, wherein the cartridge is removably coupled to the delivery tool.

6. The medical device of claim 1, wherein the cartridge has a first end portion and a second end portion opposite the first end portion, the first end portion being disposed on a surface outside of the delivery tool and the second end portion being disposed on a surface inside of the delivery tool.

7. The medical device of claim 1, wherein the biasing member is configured to move the plurality of anchors that are disposed within the cavity of the cartridge.

8. A medical device, comprising:
a delivery tool having a distal end portion, and a carrier member, the distal end portion defining a carrier opening, the delivery tool including a catch removably coupled to the distal end portion, the catch being disposed proximally from the carrier opening, the carrier member configured to move along a travel path from a position within the distal end portion, out of the carrier opening, and into a portion of the catch, at least a portion of the carrier member being curved, at least a portion of the travel path being curved, the distal end portion defining a slot;
a cartridge coupled to the distal end portion of the delivery tool, the cartridge having a base member and a coupling member that extends orthogonally to the base member, the base member of the cartridge being configured to be inserted into the slot of the distal end portion of the delivery tool, the cartridge defining an opening, the opening of the cartridge being disposed within the travel path of the carrier member; and
an anchor disposed within the cartridge, the anchor defining a lumen, the anchor being attached to the catch via an attachment member, the cartridge including a biasing member, the biasing member being disposed within a cavity of the cartridge, the biasing member being disposed proximally of the opening of the cartridge,
wherein the distal end portion of the delivery tool includes a projection, the coupling member of the cartridge includes an aperture, the projection being configured to at least partially extend into the aperture to couple the cartridge to the delivery tool,
wherein the cartridge is coupled to the delivery tool such that a portion of the travel path of the carrier member is disposed between the biasing member of the cartridge and the projection of the delivery tool,
wherein the carrier member is configured to extend through the lumen of the anchor, through the opening of the cartridge, and through bodily tissue in response to the carrier member moving along the travel path and,
wherein the catch, the anchor, and the attachment member are configured to collectively form a loop about an implant and bodily tissue in response to the carrier member moving along the travel path.

9. The medical device of claim 8, wherein the distal end portion of the delivery tool defines a curved opening, the cartridge being disposed within the curved opening when the cartridge is disposed within the slot of the distal end portion.

10. The medical device of claim 8, wherein the cartridge is configured to retain the anchor, the cartridge being configured to be removably coupled to the delivery tool.

11. The medical device of claim 8, wherein the attachment member is a suture, the suture having a first end portion coupled to the anchor and a second end portion coupled to the catch.

* * * * *